United States Patent
Berner et al.

(10) Patent No.: US 10,434,150 B2
(45) Date of Patent: Oct. 8, 2019

(54) METHODS AND PHARMACEUTICAL COMPOSITIONS FOR TREATING CELIAC DISEASE AND GLUTEN INTOLERANCE

(71) Applicant: ALVINE PHARMACEUTICALS, INC., San Carlos, CA (US)

(72) Inventors: Bret Berner, Half Moon Bay, CA (US); Matthew John Siegel, Menlo Park, CA (US)

(73) Assignee: Immunogenics LLC, Newport Beach, CA (US)

( * ) Notice: Subject to any disclaimer, the term of this patent is extended or adjusted under 35 U.S.C. 154(b) by 526 days.

(21) Appl. No.: 14/762,423

(22) PCT Filed: Jan. 23, 2014

(86) PCT No.: PCT/US2014/012809
§ 371 (c)(1),
(2) Date: Jul. 21, 2015

(87) PCT Pub. No.: WO2014/116871
PCT Pub. Date: Jul. 31, 2014

(65) Prior Publication Data
US 2015/0352195 A1    Dec. 10, 2015

Related U.S. Application Data

(60) Provisional application No. 61/755,583, filed on Jan. 23, 2013.

(51) Int. Cl.
| | | |
|---|---|---|
| A61K 38/48 | (2006.01) |
| A61K 47/22 | (2006.01) |
| A61K 9/00 | (2006.01) |
| A61K 9/20 | (2006.01) |
| A61K 47/12 | (2006.01) |
| A61K 47/18 | (2017.01) |
| A61K 47/26 | (2006.01) |
| A61K 9/08 | (2006.01) |
| A23L 33/10 | (2016.01) |
| C12N 9/50 | (2006.01) |

(52) U.S. Cl.
CPC .......... *A61K 38/4873* (2013.01); *A23L 33/10* (2016.08); *A61K 9/0053* (2013.01); *A61K 9/0095* (2013.01); *A61K 9/08* (2013.01); *A61K 9/2018* (2013.01); *A61K 38/482* (2013.01); *A61K 47/12* (2013.01); *A61K 47/183* (2013.01); *A61K 47/186* (2013.01); *A61K 47/22* (2013.01); *A61K 47/26* (2013.01); *A23V 2002/00* (2013.01); *C12N 9/50* (2013.01); *C12Y 304/21026* (2013.01); *C12Y 304/22* (2013.01)

(58) Field of Classification Search
None
See application file for complete search history.

(56) References Cited

U.S. PATENT DOCUMENTS

| | | | |
|---|---|---|---|
| 7,303,871 B2 | 12/2007 | Hausch et al. |
| 2011/0236369 A1 | 9/2011 | Berner |
| 2011/0257087 A1* | 10/2011 | Krul .............. A23C 9/1526 |
| | | | 514/4.9 |

FOREIGN PATENT DOCUMENTS

| | | |
|---|---|---|
| WO | 2010021752 | 2/2010 |
| WO | 2011097266 | 8/2011 |
| WO | 2013/016427 A1 | 1/2013 |

OTHER PUBLICATIONS

Buffer table From Ruzin, 1999. Plant Microtechnique and Microscopy, downloaded on Mar. 23, 2018 from http://microscopy.berkeley.edu/Resources/instruction/buffers.html.*
Gass et al., "Combination Enzyme Therapy for Gastric Digestion of Dietary Gluten in Patients With Celiac Sprue", Gastroenterology, Aug. 3, 2007, pp. 472-480, vol. 133., No. 2. Elsevier, Amsterdam, Netherlands.
Siegel et al., "Safety, Tolerability, and Activity of ALV003: Results from Two Phase 1 Single, Escalating-Dose Clinical Trials", Digestive Diseases and Sciences, Feb. 2012, pp. 440-450, vol. 57, Issue 2, Springer, Berlin, Germany.

* cited by examiner

*Primary Examiner* — Allison M Fox
*Assistant Examiner* — Qing Xu
(74) *Attorney, Agent, or Firm* — Pamela Sherwood; Bozicevic, Field & Francis LLP

(57) ABSTRACT

Oral administration of ALV003 can protect celiac disease patients and patients otherwise suffering from gluten-intolerance from the harmful effects of ingesting food containing gluten.

4 Claims, 6 Drawing Sheets
Specification includes a Sequence Listing.

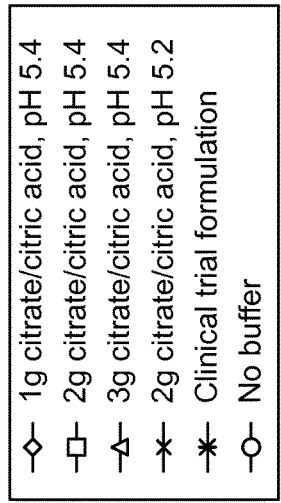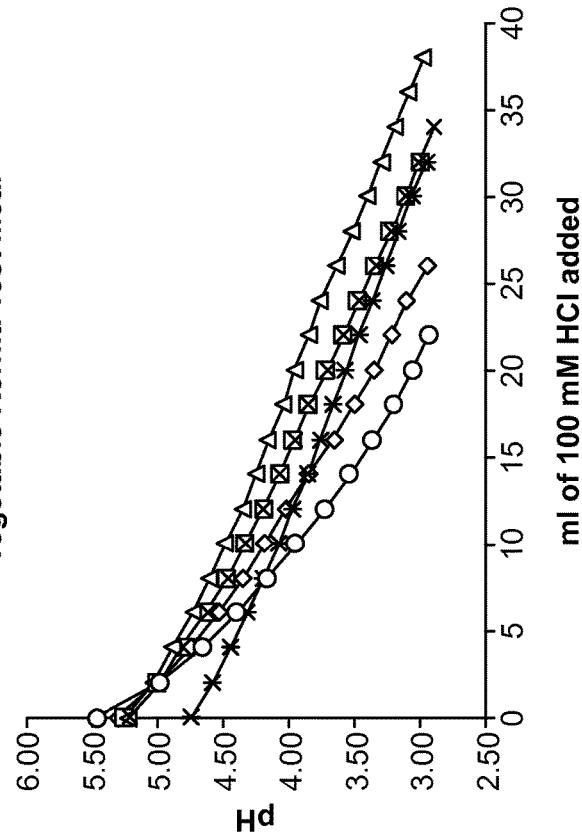
FIG. 2
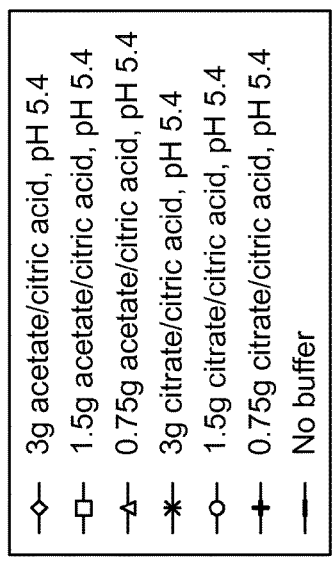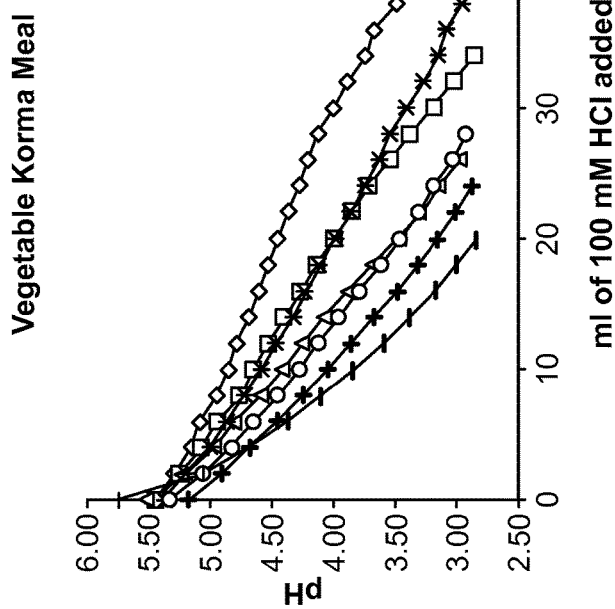
FIG. 1

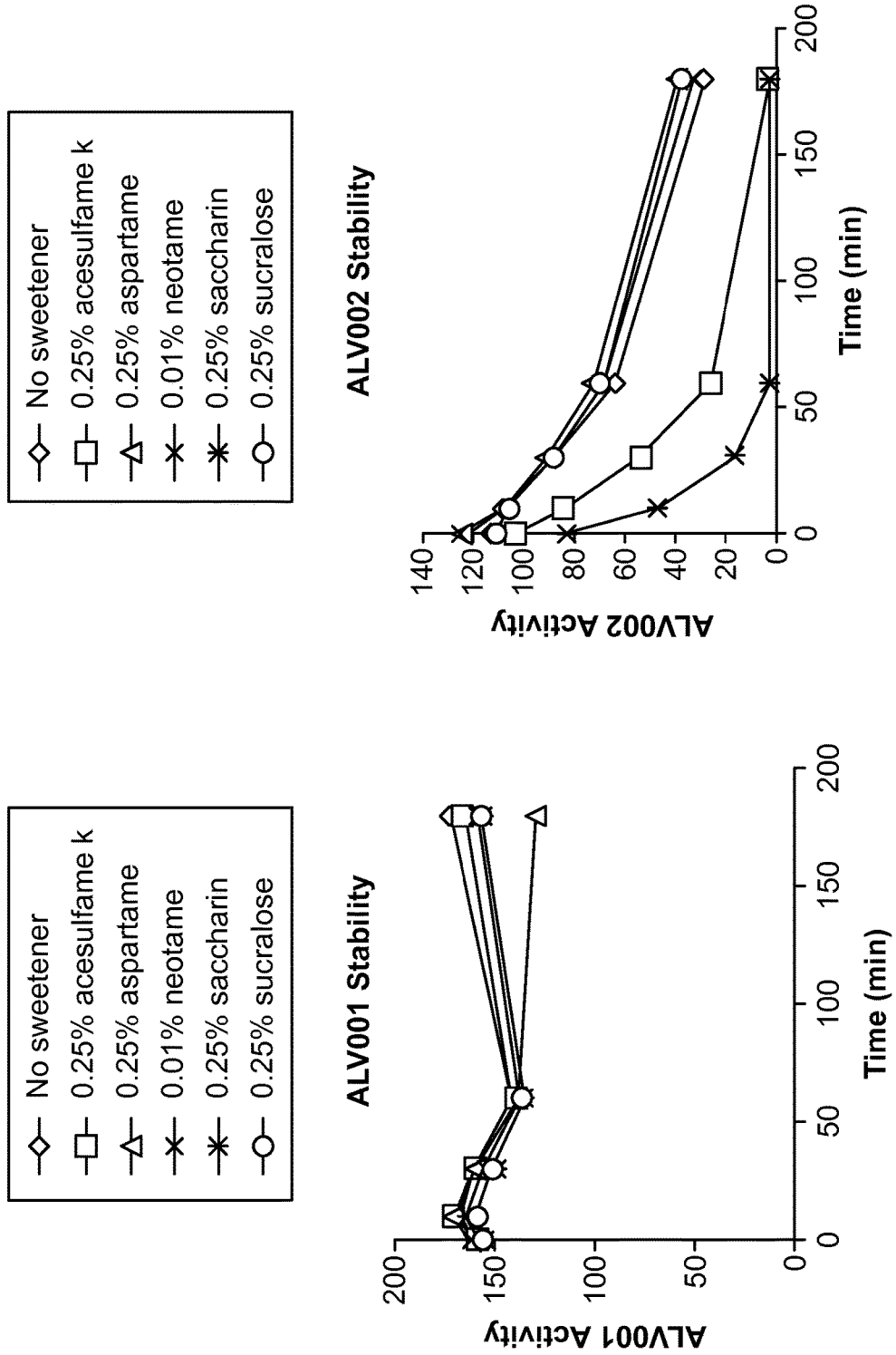

METHODS AND PHARMACEUTICAL COMPOSITIONS FOR TREATING CELIAC DISEASE AND GLUTEN INTOLERANCE

FIELD OF THE INVENTION

This invention concerns methods and compositions for protecting a subject in need from a deleterious effect of gluten ingestion. The invention specifically concerns the treatment of celiac disease and gluten intolerance. The invention further provides pharmaceutical compositions for protecting a subject in need from a deleterious effect of gluten ingestion, and, in particular, for treating celiac disease and gluten intolerance.

BACKGROUND OF THE INVENTION

Celiac Disease

Celiac disease is an acquired chronic immune disorder that develops in susceptible individuals (many of whom are of HLA genotype DQ2 or DQ8) related to an environmental factor, gluten, which is the storage protein of wheat and related grains like rye and barley. The gluten-induced small bowel pathology in celiac disease is characterized by an inflammatory reaction that is accompanied by villus atrophy and hypertrophy of crypts. Celiac disease has a wide range of clinical manifestations including latent or silent celiac disease, disease with only mild gastrointestinal disturbances, chronic gastrointestinal symptoms, malabsorption, and/or weight loss. Celiac disease is often diagnosed in patients with isolated iron deficiency anemia.

The ingestion of gluten-containing cereals can also induce manifestations outside the gut, such as osteoporosis, peripheral and central nervous system involvement, mild or severe liver disease, infertility problems, and the classical example is the gluten-induced skin disease, dermatitis herpetiformis (DH). DH is a cutaneous manifestation of celiac disease in which an intensely pruritic, herpetiform rash can present on the elbows, knees, buttocks, and scalp of a celiac disease patient in response to ingestion of gluten. The rash is characterized by high IgA deposits seen histologically in the upper papillary dermis. The symptoms and histology of the rash improve with adherence to a gluten free diet. Approximately 10% of patients diagnosed with celiac disease will manifest DH.

The only accepted standard for celiac disease diagnosis is the finding of gluten-induced small intestinal mucosal injury. Clinical findings are usually equivocal: newly diagnosed patients eating normal gluten-containing food may be totally symptomless or have only vague gastrointestinal symptoms, whereas in others symptoms may be severe; in people with extra-intestinal manifestations, gastrointestinal symptoms may also be absent. One feature that is common to all however is the manifest gluten-sensitive small intestinal mucosal lesion. In untreated celiac disease, the length of functionally impaired bowel determines the degree of malabsorption, and the presence of symptoms does not relate at all to the histological features of the proximal biopsy. During the last two decades, highly sensitive and specific gluten-dependent serum autoantibody tests have been used for celiac disease case finding, population-based screening studies, monitoring the gluten-free diet, and measurement of mucosal relapse on gluten challenge.

For patients with celiac disease, lifelong complete gluten exclusion needs to be followed strictly to avoid a substantially enhanced risk for the development of further complications, such as bone disorders, infertility, and cancer. The mortality rate in patients with celiac disease exceeds that of the general population; however, there is a trend towards reduction in mortality after 1-5 years on a gluten-free diet.

Following a completely gluten-free diet is, however, very challenging. Even highly motivated patients who try to maintain a strict dietary regimen are affected due to inadvertent or background exposure to gluten (FDA 2006). As many as 80% of patients with celiac disease who are in clinical remission, and who claim to be following a gluten-free diet, have persistent abnormalities in small bowel biopsy specimens. Inadvertent exposure to gluten has been identified as the leading cause of non-responsive celiac disease among clinically diagnosed patients who were presumed to be on a gluten-free diet. A gluten-free diet is more expensive than a so-called 'normal' diet, which can make adherence to the diet difficult; also social life and travel contribute to dietary lapses. Taken together, there is an acute need for non-dietary therapies for celiac disease.

Time-course studies of gluten challenges provide clear evidence of an inflammatory process, as there is a dose-dependent accumulation of lymphocytes to the epithelium during the lower-dose gluten challenges. Upon further challenge, crypt hyperplasia occurs, and lastly, villus effacement is seen (flat mucosal lesion). As evidenced in clinical practice with patients having silent celiac disease, the mucosal deterioration upon gluten challenge is often seen before clinical symptoms occur. In one study challenging adolescent and young adult celiac patients with 10 g of gluten per day, a control small intestinal biopsy at the time of seroconversion of the celiac-type autoantibodies showed that the gut mucosa relapsed in 70% of the patients before clinical symptoms occurred. Thus, gluten-induced damage in the small intestinal mucosa is a prerequisite for symptoms and complications of celiac disease, some of which may occur only years or decades after starting gluten ingestion.

In celiac disease, the onset of symptoms and signs of gluten intolerance may occur in childhood but become evident only in adulthood or in the elderly after decades of gluten ingestion. People eating an average Western diet ingest approximately 15-25 g gluten per day. Previous clinical gluten challenge studies show that older children, adolescents, and young adults with long-term treated celiac disease can tolerate well the ingestion of 10-20 g gluten per day. Also, a gluten challenge with repeated small intestinal mucosal biopsies has until fairly recently been mandatory to establish the definite diagnosis of celiac disease, especially in children (in some parts of the world this regimen is still followed). The effect of small gluten loads on the mucosal integrity and a safe gluten threshold in treated celiac disease is still under discussion. The literature indicates that doses of 1.5 to 2 g of gluten per day should cause some deterioration and inflammation but without inducing too many clinical symptoms and causing severe side effects. One and a half grams to 2 g of daily gluten exposure corresponds to the ingestion of approximately one-half to two-thirds a slice of wheat flour-based bread per day. A drug, to be clinically effective, should be able to reduce significantly or prevent the mucosal deterioration caused by a daily gluten challenge.

The only currently available treatment option for celiac disease patients is complete exclusion of dietary gluten; however, because gluten is found ubiquitously in the food supply, strict avoidance is extraordinarily difficult if not impossible for most patients. Because of ongoing gluten exposure, celiac disease patients (even when attempting to adhere to a gluten-free diet) suffer from the consequences of continued gluten exposure, including a significant increase in associated morbidity and mortality. Taken together, these observations establish that celiac disease represents a serious unmet medical need; therefore, a therapeutic intervention that could serve as an adjunct to an attempted gluten-free diet to attenuate or eliminate the pro-inflammatory, immunogenic potential of gluten in celiac disease patients would be a major clinical advance in the treatment of this disease. The ultimate goal in celiac disease clinical research is to prevent disease and sustain health and to provide new therapeutic strategies that are less burdensome than a strict life-long gluten-free diet. A long term goal is a therapy that would allow celiac disease patients to be able to ingest foods containing wheat, barley, and/or rye safely. A drug for the treatment of celiac disease should be able to prevent gluten-induced mucosal injury. Only then will celiac experts, advisors for celiac support groups, and patient organizations, accept the drug as an adjunct therapy or alternative treatment to strict gluten-free diet.

Proteases for the Treatment of Celiac Disease

A promising new approach to treating celiac disease involves the oral administration of proteases, called glutenases, which can degrade gluten. See PCT Pat. Pub. No. 2003/068170; 2005/107786; 2007/044906; 2007/047303; 2008/115411; 2010/021752; and 2013/016427; and U.S. Pat. Nos. 7,303,871; 7,320,788; 7,628,985; 7,910,541; and 7,943,312, each of which is expressly incorporated herein by reference.

Cysteine endoprotease (EP) B2 (also known as EPB2), a barley derived protease, and other similar proteases derived from the germinating seeds of the gluten-containing cereals have been identified as effective agents for the detoxification of gluten, the causative agent in celiac disease (see U.S. Pat. Nos. 7,303,871 and 7,320,788; U.S. Pat. App. Pub. Nos. 20100092451 and 20110171201; and PCT Pub. 2013/016427). A modified, recombinant form of the barley-derived EPB2 zymogen called "ALV001" (the active form of this enzyme is termed "ALV001*" herein) has been used as part of a combination enzyme therapy (including a prolyl endopeptidase (PEP), such as *Sphingomonas capsulata* PEP) for oral administration to celiac disease patients to aid in the digestion of gluten before it can exert its toxic effects in these patients (see U.S. Pat. No. 7,320,788; U.S. Pat. App. Pub. No. 20080193436; PCT Patent Pub. Nos. 2008/115428; 2008/115411; 2010/021752; 2010/042203 and 2013/016427, each of which is expressly incorporated herein by reference). The ALV001 zymogen becomes active (converts to ALV001*) below pH 5, but is not activated at a higher pH.

ALV003 is an especially promising new drug in clinical development that is a mixture of two glutenases: *Sphingomonas capsulata* prolyl endopeptidase and ALV001 (or ALV001*). See PCT Pat. Pub. Nos. 2005/107786; 2008/115428; 2008/115411; 2010/021752; 2010/042203; and 2013/016427, each of which is expressly incorporated herein by reference. Oral glutenases such as ALV003 help to proteolyze the immunoreactive gluten peptides present in food before they can trigger an immune response in the intestinal mucosa. There remains a need for new methods and pharmaceutical compositions that can be used to protect celiac disease patients and other individuals suffering from gluten intolerance from the harmful effects of inadvertent exposure to gluten and to make gluten ingestion safer for them. The present invention meets these needs.

SUMMARY OF THE INVENTION

In a first aspect, the present invention provides new pharmaceutical compositions of ALV001 and/or ALV001*, ALV002, and ALV003 (an orally administered, fixed dose (1:1 ratio by weight) combination of ALV001 and/or ALV001* and ALV002; see PCT Pub. Nos. 2008/115411 and 2013/016427, each of which is incorporated herein by reference), and new unit dose forms containing such compositions.

In one embodiment, the components of the ALV003 drug product are packaged separately into (i) an ALV001 or ALV001* drug product; (ii) an ALV002 drug product; and (iii) flavoring and additional excipients. In one embodiment, these three separate packages are in the form of a stick pack or sachet containing the drug product and/or excipients/flavorings in powdered form. Prior to ingestion, the patient dissolves the contents of the three packages into an aqueous solution (typically, water), which is then consumed by the patient. Illustrative embodiments of these drug products are provided in the examples below.

In another embodiment, the components of the ALV003 product are packaged separately into (i) an ALV003 drug product (containing both ALV001 or ALV001* and ALV002); and (ii) flavoring and additional excipients. In one embodiment, these two separate packages are in the form of a stick pack or sachet containing the drug product and/or excipients/flavorings in powdered form. Prior to ingestion, the patient dissolves the contents of the two packages into an aqueous solution (typically, water), which is then consumed by the patient. Illustrative embodiments of these drug products are provided in the examples below.

The present invention arose in part from the discovery that ALV003 activity (the activity of both the ALV001* and ALV002 enzymes) could be enhanced by ensuring that the liquid dosage form ingested by the patient would have a pH in the range of 4 to about 6 and that the pH of the patient's stomach contents would remain in this range for a period of from about 5 to at least about 30 or more minutes after ingestion of the liquid dosage form. While a variety of buffering systems can be employed, suitable buffering systems include: citrate/citric acid; fumaric acid/fumarate; acetate/acetic acid; maleate/maleic acid; and malate/malic acid, as well as combinations of these systems. Further, in accordance with the invention, if a buffering system containing sodium is employed, the amount of buffer needed to ensure this pH range is maintained for the desired period of time may result in a high sodium dose, which can be undesirable for certain patients. Thus, in some embodiments, the invention provides for the use of potassium salts, in place of some or all of the sodium salts, to avoid this problem. In various embodiments, the total amount of sodium in a single dose of ALV003 is no more than 800 mg per dose. In some embodiments, the total amount of sodium in a single dose of ALV003 is no more than 500 mg per dose. In some embodiments, the total amount of sodium in a single dose of ALV003 is no more than about 375 mg per dose.

The present invention also arose from the discovery that hygroscopic materials, including potassium salts, cysteine, and flavoring agents, could unfavorably affect stability and activity of the ALV003 enzymes. Thus, in various embodiments of the drug products of the invention, any hygroscopic excipients are packaged separately or isolated from the two enzymes in the ALV003 drug product or dried and handled under very low relative humidity conditions, i.e., at least less than 15% RH.

The present invention also arose from the discovery that certain sweeteners have a negative effect on ALV002 activity. The sweeteners sucralose, aspartame, and neotame do not have such a negative effect and so are employed in various embodiments of the drug products of the invention.

In one embodiment of the drug products of the invention, the ALV001 drug product (unless otherwise indicated, reference to the "ALV001 drug product" refers to any drug product of the invention that comprises either the ALV001 proenzyme and/or its active form ALV001*) and comprises the excipients sodium citrate, citric acid, and/or sodium metabisulfite. In various embodiments, the ALV001 drug product further comprises mannitol, TRIS base, TRIS hydrochloride, EDTA, and/or monothioglycerol. In one embodiment of the drug products of the invention, the ALV002 drug product comprises the ALV002 enzyme and the excipients sodium citrate, and citric acid. In various embodiments, the ALV002 drug product further comprises mannitol, TRIS base, TRIS hydrochloride, EDTA, and monothioglycerol. In one embodiment of the drug products of the invention, the ALV001 drug product and the ALV002 drug product are admixed together. In one embodiment of the drug products of the invention, the flavoring and additional excipients (which may be the same or different excipients from those in the ALV001 drug product and ALV002 drug product) are separately packaged and comprise potassium citrate, citric acid, cysteine, sucralose and/or aspartame and/or neotame, and one or more flavorings. Optionally, the cysteine is coated for taste masking.

In one embodiment, a patient in need of treatment for a condition as described herein is administered a daily dose of ALV003, which dose may be delivered by administration of an admixture of ALV001 and/or ALV001* and ALV002, ranging from 50 mg to 3 g per day of each enzyme. The daily dose may be subdivided into two, three, or more separate doses ("subdivided daily dose"). The daily dose or each subdivided daily dose is taken with a meal. As used herein, "with a meal" includes taking the ALV003 dose within 30 minutes or less, i.e., 15 or 20 minutes, of initiating consumption of the meal, during consumption of the meal, and within 30 minutes after consumption of the meal. In various embodiments, the ALV003 dose will be administered at the start of consumption or after consuming some, but typically no more than half, of the meal. Patients can take a dose or subdivided daily dose with any meal, with every meal, with meals known to or suspected by the patient to contain gluten, and/or with meals unknown to the patient to contain gluten. Patients may consume all or any portion of a unit dose during a meal, i.e., the unit dose of ALV003 may be consumed all at once or in portions during the meal. Patients can maintain therapy for any period, such as a day, a week, a month, a year, a decade, and their entire life. Intermittent therapy can also be practiced by the patient.

Patients with conditions suitable for treatment in accordance with the invention include: celiac disease (which includes Celiac sprue and/or dermatitis herpetiformis) patients, including patients with active disease and patients with disease in remission; patients requiring protection from a sign or symptom of celiac disease, including but not limited to a skin lesion or intestinal mucosal injury due to gluten ingestion up to 250 mg, 500 mg, 1 g, 2 g, 3 g, 5 g, 10 g, or 25 g or more gluten per day; patients who need therapy for an existing sign or symptom of celiac disease, including but not limited to a skin lesion or intestinal mucosal injury due to gluten ingestion up to 250 mg, 500 mg, 1 g, 2 g, 3 g, 5 g, 10 g, or 25 g or more gluten per day; undiagnosed celiac disease; patients with gluten-intolerance; and persons simply wishing to avoid gluten ingestion and accelerate digestion of any gluten ingested from their diet. In some embodiments, the patient needs therapy for an existing intestinal mucosal injury, and treatment results in healing as evidenced by improvement in the patient's Villus height:Crypt depth (Vh:Cd).

Without limitation, the invention includes the following particular aspects and embodiments.

In one aspect, the invention concerns a method for protecting a patient from a deleterious effect of gluten ingestion, said method comprising administering to the patient a dose of ALV003 sufficient to prevent said deleterious effect. In another aspect, the invention concerns a method for preventing signs or symptoms of celiac disease in a celiac disease patient ingesting gluten, the method comprising orally administering ALV003 in an amount ranging from 100 mg to 6 g per day. In another aspect, the invention concerns use of ALV003 in the preparation of a medicament for protecting a patient from a deleterious effect of gluten ingestion, by administering to said patient a dose of ALV003 sufficient to prevent said deleterious effect. In yet another aspect, the invention concerns use of ALV003 in the preparation of a medicament for preventing signs or symptoms of celiac disease in a celiac disease patient ingesting gluten, by orally administering ALV003 in an amount ranging from 100 mg to 6 g per day. In a further aspect, the invention concerns ALV003 for use in protecting a patient from a deleterious effect of gluten ingestion, by administering to said patient a dose of ALV003 sufficient to prevent said deleterious effect. In a still further aspect, the invention concerns ALV003 for use in preventing signs or symptoms of celiac disease in a celiac disease patient ingesting gluten, by orally administering ALV003 in an amount ranging from 100 mg to 6 g per day. In any of the above aspects, in one embodiment, the patient is administered an ALV003 dose in the range of 100 mg to 1.5 g with a meal.

In a different aspect, the invention concerns a kit comprising ALV003 in a container and a label affixed to or instructions associated with the container directing administration of said ALV003 to protect a patient from a deleterious effect of gluten ingestion. In a further aspect, the invention concerns a kit comprising ALV003 in a container and a label affixed to or instructions associated with the container directing administration of said ALV003 to prevent signs or symptoms of celiac disease in a celiac disease patient ingesting gluten, by orally administering ALV003 in an amount ranging from 100 mg to 5 g per day. The invention encompasses a method for protecting a patient from a deleterious effect of gluten ingestion, the method comprising administering to the patient a dose of ALV003 sufficient to prevent said deleterious effect. In this and any of the foregoing embodiments, the ALV003 may be in a form in which the ALV001 (or ALV001*) is in a separate dosage form from the ALV002 or in a form in which the ALV001 (or ALV001*) and ALV002 are admixed or otherwise combined in a single unit dosage form. In various embodiments, the kit includes one or more flavor packs. In various embodiments, the flavor packs contain one or more hygroscopic excipients, including but not limited to cysteine and potassium citrate.

The embodiments herein are equally applicable to all aspects of the invention, including the particular aspects enumerated above.

In one embodiment, the patient has celiac disease, and said deleterious effect is intestinal mucosal injury. In another embodiment, the patient has symptomatic celiac disease. In yet another embodiment, the patient is moderately to severely symptomatic. In a further embodiment, the patient has experienced symptoms of celiac disease, ranging from moderate to severe, within one month prior to said first administration. In certain embodiments, the symptoms are self-reported, where the patient may report, for example, symptoms with a severity score of at least 3 on a 0-10 numeric rating scale of severity, or with a severity score of at least 4 on a 0-10 numeric rating scale of severity. In various embodiments, the signs or symptoms of celiac disease comprise one or more of diarrhea, constipation, abdominal pain, bloating, nausea, fatigue, and skin rash.

In other embodiments, the serology status of the patient is determined prior to administration, where determination of the serology status may comprise, without limitation, an antibody test selected from the group consisting of anti-gliadin antibodies (AGA), anti-reticulin antibodies (ARA), IgA anti-human tissue transglutaminase (TTG) antibodies (TG2), IgA anti-endomysial antibodies (EMA), and anti-deamidated gliadin peptide (DPG) tests. In a further embodiment, the patient does not exhibit IgE-mediated reaction to wheat.

In various embodiments, administration may occur at mealtime, such as with a major meal, for example, with major meals of at least one to three times per day. In various embodiments, administration may occur at any time food suspected of containing gluten is ingested by the patient. In other embodiments, the ALV003 dose administered may, for example, be in the range of 100 mg to 2 g per administration, e.g., 100 mg per administration, 300 mg per administration, 600 mg per administration, 900 mg per administration, or 1200 mg per administration. In further embodiments, the dose may be administered at least once a day for at least a month, for at least 300 days per year, for at least two years, or for the rest of the patient's life.

In one embodiment, each dose of ALV003 comprises a dose of ALV001 and/or ALV001* in powdered form and a dose of ALV002 in powdered form, and a dose of additional excipients and flavoring(s) in powdered form, and said powders are dissolved in a potable liquid to be ingested by said patient. In one embodiment, the ALV001 (or ALV001*) and ALV002 are in separate unit dose forms, and there is a third dose form comprising one or more of a flavoring, a sweetener, a hygroscopic material. In one embodiment, the ALV001 (or ALV001*) and ALV002 are admixed together to provide a unit dose form, and there is a second dose form comprising one or more of a flavoring, a sweetener, and a hygroscopic material, including but not limited to potassium citrate and/or cysteine.

In various embodiments, the ALV003 dose is administered with food containing at least 20 mg but not more than 25 g of gluten, or with food containing no more than about 1 g of gluten, or with food containing no more than about 2 g of gluten, or with food containing no more than about 3 g of gluten, or with food containing no more than about 5 g of gluten, or with food containing no more than about 10 g of gluten, or with food containing no more than about 15 g of gluten, or with food containing no more than about 25 g of gluten.

In a further embodiment, the ALV003 has equal amounts by weight of ALV001 and ALV002, wherein the ALV001 (when converted to ALV001*) has a specific activity of at least 5000 or more proteolytic activity units per mg, and said ALV002 has a specific activity of at least 3000 or more proteolytic activity units per mg. In various embodiments, the drug products of the invention comprise ALV001*, and in these embodiments, the propeptide that is cleaved during activation of ALV001 to ALV001* may be present, in which case the weight of the (ALV001* plus cleaved propeptide) is equal to the weight of the ALV002 in the drug product. In other embodiments, the weights of ALV001 (or ALV001*) and ALV002 may not be identical.

In a further aspect, the invention concerns a kit comprising ALV003 in a container and a label affixed to or instructions associated with the container directing administration of said ALV003 to protect a patient from a deleterious effect of gluten ingestion. In a still further aspect, the invention concerns a kit comprising ALV003 in a container and a label affixed to or instructions associated with the container directing administration of said ALV003 to prevent signs or symptoms of celiac disease in a celiac disease patient ingesting gluten, by orally administering ALV003 in an amount ranging from 100 mg to 6 g per day. In one embodiment, the kit contains at least three separate components: an ALV001 (or ALV001*) drug product component, an ALV002 drug product component, and a flavor and other excipient component. In one embodiment, the kit contains at least two separate components: an ALV001 (or ALV001*) admixed with an ALV002 drug product component, and a flavor and other excipient component. Various embodiments of such components suitable for use in such kits are described in the examples below and elsewhere herein. Any component in any example may be combined with any other component in any other example below for use in a kit of the invention. Further, any excipient in any amount exemplified in the examples below or described elsewhere herein may be used in any component.

In another aspect, the invention concerns a unit dosage form of ALV003 for oral administration. In various embodiments, the unit dosage form may, for example, be in solid form, such as, but not limited to, a tablet, including an orally disintegrating tablet, a powder or sprinkle, sachet(s), or stickpack(s) or combinations thereof comprising powdered forms of one or more ingredients, or may be in a liquid form. In various embodiments, the drug product is in a solid form, including but not limited to a solid form described above, but is dissolved in a potable liquid, such as water, prior to administration to the patient. In such embodiments, the liquid form prepared in accordance with the instructions that accompany the drug product in solid form, is a liquid drug product of the invention. In various embodiments, the unit dosage form consists of three packages, stickpacks, or sachets: one containing ALV001 and/or ALV001* (but in many embodiments containing only ALV001*), one containing ALV002, and a third containing additional excipients and flavoring(s). In other embodiments the unit dose consists of two packages, stickpacks, or sachets: one containing ALV001 and/or ALV001* (but in many embodiments containing only ALV001*) and ALV002, and a second containing additional excipients and flavoring(s). In various embodiments, hygroscopic excipients and flavoring(s) are contained in a separate package, stickpack, or sachet.

Thus, the unit dosage form may comprise one or more sachets or stickpacks comprising a powdered form of ALV001 and/or ALV001* and/or ALV002 and/or additional excipients and flavorings. In one embodiment, the unit dosage form comprises ALV001 and/or ALV001* and ALV002 in the same sachet, stickpack, orally disintegrating tablet, powder, or sprinkle. In another embodiment, the unit dosage form comprises ALV001 and/or ALV001* and ALV002 in separate sachets, stickpacks, orally disintegrating tablets, powders, or sprinkles. In other embodiments, the unit dosage form may further comprise a flavor agent or agents, which may, for example, be contained in a sachet comprising ALV001 and/or ALV001* and/or ALV002, or may be formulated separately, e.g. in a separate sachet, stickpack, orally disintegrating tablet, powder, or sprinkle.

Optionally, the unit dosage forms may contain instructions for dilution of the powder or powders contained in the sachet(s), stickpack(s), orally disintegrating tablet(s), powder(s), or sprinkle(s), which may be dissolved in a potable liquid and reconstituted as a drink. The potable liquid may, for example, be water or fruit juice. In one embodiment, a sachet or stickpack containing flavoring, buffers to maintain the pH between 4 and 6, sweeteners, or other excipients may be added to the potable liquid. In one embodiment, the patient is instructed to dissolve the flavoring unit dose in solid form in a potable liquid prior to dissolving the ALV001* (or ALV001) and ALV002 enzyme containing solid dose forms therein. In one embodiment where the dosage forms are sprinkles, the sprinkles may be mixed with or put on food.

In one embodiment, the sum of all the buffers in the stickpack(s) are sufficient to maintain the pH in the solution for oral administration and in a simulated in vitro model stomach (or in the stomach in vivo) between pH 4 and pH 6, and more typically between 4.5 and 5.5, or between 5.0 and 5.5, such as 5.1-5.2, for at least 15 minutes, or at least 30 minutes, or at least an hour. To achieve this buffering capacity for this period of time, the quantity of buffer in all combined drug product packages may be between 0.15 g and 5 g, and preferably between 0.5 and 4 g, and still more preferably between 0.75 and 3.5 g. Alternatively, between at least 0.5 millimoles and 20 millimoles of the aforementioned buffer, preferably between 1.5 and 15 millimoles and more preferably between 2.5 and 12 millimoles, is included combined for all packaged drug components. Suitable buffers may include, but are not limited to, citrate, acetate, succinate, maleate, fumarate, malate, sorbate, tartrate, glycerophosphate, or lactate. Sodium, potassium, and/or calcium are the preferred counterions for the salts.

In various embodiments, the buffer is a citrate buffer, and the ALV003 drug product contains citric acid, sodium citrate, and potassium citrate in an amount, collectively, ranging, per dose, from at least 300 mg to about 3 g. Illustrative unit dose forms of the invention contain about 500 mg, about 1 g, about 1.5 g, about 2 g, and about 3 g of citric acid buffer, where citric acid buffer is composed of citric acid, sodium citrate, and potassium citrate and provides the buffering capacity described in the immediate prior paragraph and elsewhere herein. In any of the aforementioned embodiments, the unit dose form may contain no more than 1 g or no more than 500 mg or no more than 250 mg of sodium citrate, and the remaining citrate in the dose form is provided in the form of potassium citrate. In various embodiments, the potassium citrate is contained in a dose form that does not contain any ALV001* (or ALV001) or ALV002, i.e., it is contained in the flavor packet. In various embodiments, the potassium citrate is contained in a dose form that also comprises cysteine, a flavoring, and/or sweetener. In various embodiments, the sweetener is sucralose, aspartame, or neotame.

In one embodiment a stickpack, sachet or tablet contains flavoring(s). Any flavoring(s) suitable for food or pharmaceutical industries can be used.

In one embodiment, the dosage form, whether stickpack(s), sachet(s), or tablet(s) may contain a sweetener, which sweetener may be a sugar, unrefined sweeteners, which are made from fruit or sap plants, sugar alcohols, xylitol, erythritol, lactitol, maltitol, mannitol, sorbitol, mogrosides, glycerol, glycerrhizin, hydrogenated starch lysates, isomalt, brazzein, curculin, monelin, or other artificial sweeteners such as aspartame, Na aspartame, K acesulfame, neotame, stevia, sucralose, saccharin, cyclamate, neohesperidin dihydrochalcone, or other sweeteners. Sweeteners, such as those above, may be used between 0.01% and 5% of the volume of water to be added, for example, for 100 ml water to drink at 0.01% sweetener, the formulation comprises 10 mg of sweetener in the stickpacks; or for 200 ml water to drink at 0.025% sucralose, the formulation comprises 50 mg sucralose in the stickpacks, and the like. In those embodiments in which the excipient cysteine is present in the drug product in a form that is not taste masked, more sweetener (and/or flavoring) may be used; correspondingly, if the cysteine is coated or otherwise treated to mask it's taste, less sweetener (and/or flavoring) may be used.

The dosage form may be sachet(s), stickpack(s), tablet(s), sprinkles, orally disintegrating tablet, or other suitable oral dosage form.

In one of the embodiments, the more hygroscopic excipients, such as cysteine and potassium citrate are isolated from the ALV001 and/or ALV001* and optionally the ALV002 either through coating of the active agent or excipient in a water dissolvable coating, or through packaging in other stickpacks, sachets, tablets, or tablet layers, such as a bilayer or trilayer tablet. In preferred embodiments, hygroscopic antioxidants, buffer salts, or other excipients are incorporated into the flavor sachet or stickpack, or the flavor and the ALV002 stickpacks.

Where separate stickpacks are used, these stickpacks may be attached for convenience by heat seals or other means between the two or more stickpacks. These heat seals may be meant to stay intact unless cut or may be designed to be burstable by the user to allow mixing of the stickpacks prior to dispensing.

In some embodiments a unit dosage form of ALV003 comprises from 50 mg to no more than 750 mg of ALV001*; from 50 mg to no more than 750 mg of ALV002; from 0.5 to no more than 4.9 mmoles of citric acid; from 1.4 to no more than 11 mmoles citrate; and from 0.11 to no more than 1.14 mmoles cysteine. This unit dosage form may further comprise 0.3 to 200 mg sweetener; and 25 to 1500 mg flavoring, where the sweetener is usually other than acesulfame K and saccharin. Exemplary sweeteners may include sucralose, aspartame, and neotame, for example wherein the unit dose contains from 10 to no more than 11 mg sucralose; from 5 to no more than 200 mg sodium aspartame; or from 0.3 to no more than 25 mg neotame; including specifically 20 to 65 mg sucralose. The citrate in this unit dosage form may be provided as from 0.46 to no more than 3.7 mmoles sodium citrate, and from 0 to no more than 7.3 mmoles potassium citrate. The specific activity of ALV001* is usually from 4000 to 20000 units activity/mg protein, and may be from 5000-18,500 units activity/mg protein. The specific activity of ALV002 may be from 2000 to 10000 units activity/mg protein, and may be from 2500 to 8000 units activity/mg protein. In this unit dosage form, cysteine may be provided in a separately formulated component from ALV001* and ALV002. In this unit dosage form, when potassium citrate is present, it may be provided in a separately formulated component from ALV001* and ALV002.

All embodiments can be variously combined with each other, and, as noted before, apply to all aspects of the invention.

BRIEF DESCRIPTION OF THE DRAWINGS

FIG. 1. Addition of buffer can enhance the buffering capacity in a dose dependent manner relative to the unbuffered meal.

FIG. 2. Results of a series of citrate buffers at either pH 5.4 or 5.2 ranging from 1-3 g of total buffer added to a Korma test meal.

FIGS. 5A and 5B. Stability of ALV001 and ALV002 in solutions containing artificial sweeteners, including 0.25% acesulfame potassium, 0.25% aspartame, 0.01% neotame, 0.25% saccharin, and 0.25% sucralose.

DETAILED DESCRIPTION OF THE INVENTION

Figure 3:
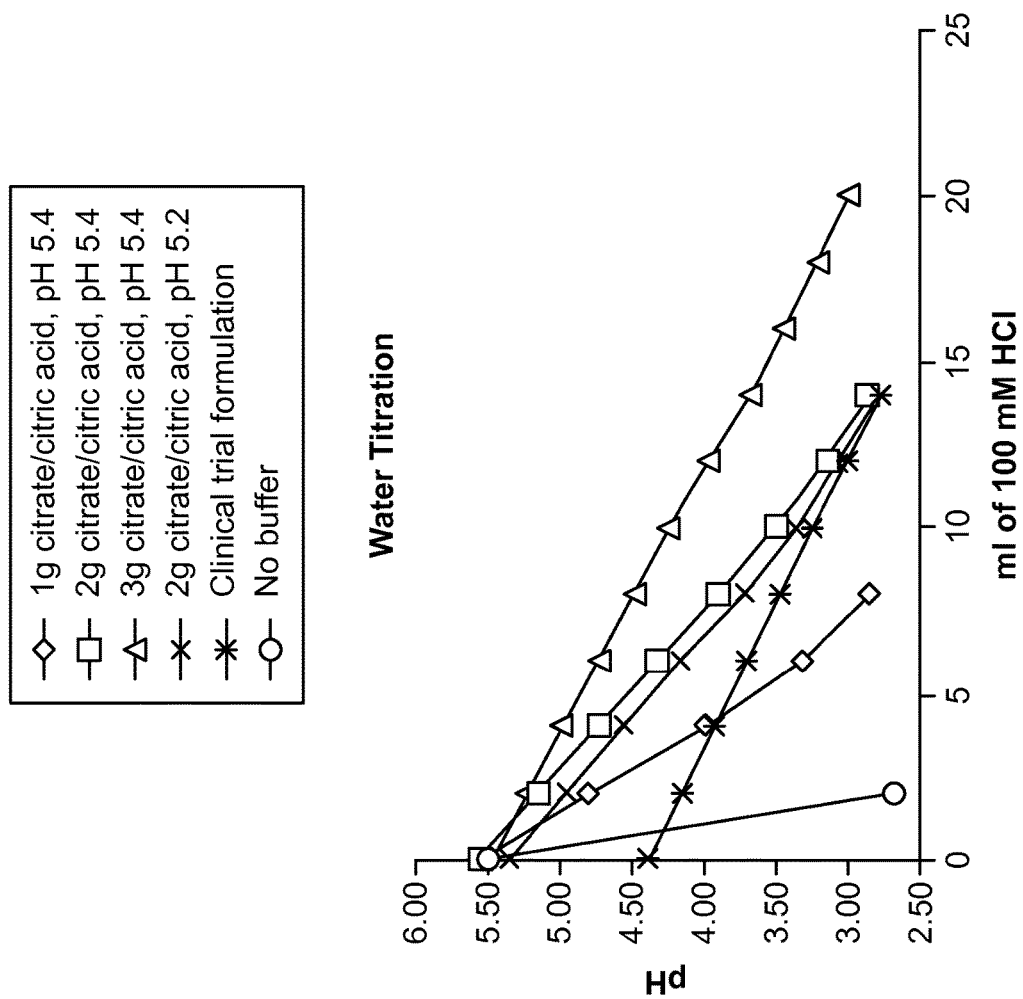
FIG. 3. Results of a series of citrate buffers at either pH 5.4 or 5.2 ranging from 1-3 g of total buffer added to a water test meal.

The term "ALV001" is used herein to refer to a zymogenic proenzyme form of cysteine endoprotease B, isoform 1 (EP-B2), naturally occurring in barley. The term, as used herein, specifically includes the 401 amino acid polypeptide provided herein as SEQ ID NO:1 and also corresponding to SEQ ID NO: 1 in PCT Patent Application No. US2012/048149 (PCT Pub. No. 2013/016427), incorporated herein by reference, with or without the highlighted, vector-derived N- and/or C-terminal residues and with and without the His tags incorporated in the N- and/or C-terminal sequences. The definition of ALV001 further includes post-translational modifications of the proenzyme. In the Examples, "ALV001" is used to refer to the recombinant form of the proenzyme.

The term "ALV001*" is used herein to refer to an active form of the proenzyme ALV-001, as hereinabove defined. The term, as used herein, specifically includes the polypeptide provided herein as SEQ ID NO:2 and also corresponding to of SEQ ID NO: 2, in PCT Patent Application No. US2012/048149 (PCT Pub. No. 2013/016427), incorporated herein by reference, with or without the highlighted vector-derived C-terminal residues and with or without the C-terminal His tags. In the Examples, "ALV001*" is used to refer to the recombinant form of the active enzyme.

The term "ALV002" is used herein to refer to a recombinant version of a prolyl endopeptidase from the bacterium *Sphingomonas capsulata* (SC-PEP). The term, as used herein, expressly includes the 741 amino acid commercial form of ALV002 provided herein as SEQ ID NO:3 and also corresponding to SEQ ID NO:3 in PCT Patent Application No. U.S. Ser. No. 12/048,149 (PCT Pub. No. 2013/016427), incorporated herein by reference, with or without the six contiguous histidine residues (hexa-His tag) added in the N-terminal region, and with or without the 38 N-terminal amino acids removed during proteolytic processing. In the Examples, "ALV002" is used to refer to the recombinant form of the enzyme.

The term "ALV003" is used herein to refer to a combination and/or co-administration of ALV-001 and ALV-002 or ALV-001* and ALV-002 or (ALV-001 and ALV-001*) and ALV-002 in a 1:1 (w/w) ratio. For purposes of determining this weight ratio, ALV-001* is attributed the same (higher) weight as ALV-001. In various embodiments, ALV-001* is present in a drug substance that contains the propeptide that was cleaved from ALV-001 to product ALV-001*. In one embodiment, ALV-001 and ALV-002 or ALV-001* and ALV-002 or (ALV-001 and ALV-001*) and ALV-002 are present in the same formulation/dosage form in 1:1 (w/w) ratio (and the formulation/dosage form may include either a formulation in which the two enzymes are admixed or otherwise combined in a single unit dosage form, or a formulation in which the two enzymes are in separate dosage forms for co-administration). Unless expressly indicated otherwise, the term "ALV-3" or "ALV003" includes combinations comprising ALV-001 and/or ALV-001*. In many embodiments, ALV-001* is used without any ALV-001. In the Examples, "ALV003" is used to refer to a combination or co-administration of the recombinant forms of ALV001 and/or ALV001* and ALV002.

The term "ALV001/ALV001*" is sometimes used herein to mean that either ALV001 or ALV001* can be used. As noted above, in many embodiments, the active form (ALV001*) of the enzyme is employed. Likewise as noted above, in calculating the weight percentages of ALV001 or ALV001* provided herein, it was assumed that the proenzyme (ALV001) form was used or that the ALV001* drug substance included the pro-peptide cleaved during the activation process.

The terms "simultaneous administration," "co-administration", and "concurrent administration" are used interchangeably and refer to the administration of at least two active agents, using separate formulations or a single pharmaceutical formulation, and consecutive administration in either order, wherein preferably there is a time period while both (or all) active agents simultaneously exert their biological activities. Thus, if ALV-001* is a first therapeutic agent, then the second therapeutic agent, such as ALV-002, may be administered prior to, contemporaneously with, or following, administration of the first therapeutic agent. In one particular embodiment, the two or more active agents (such as ALV-001 and/or ALV-001* and ALV-002) are administered to the patient the same time, in a single formulation, i.e., a single unit dosage forms, or separate formulations of the two enzymes, i.e., two different dosage forms that are administered concurrently to the patient. In many embodiments of the present invention, two or more separate solid dose forms are dissolved in liquid, which liquid is then administered to the patient. In some embodiments separate solid dose forms of ALV-001*, ALV-002, and admixed flavor/excipient/sweeteners are co-administered by dissolving them in a liquid that is then drunk by a patient.

The terms "drug product" and "drug substance" are used herein generally in accordance with the definitions provided by 21 C.F.R. 314.3. A drug substance comprises an active ingredient (such as ALV001* or ALV002) that is intended to furnish pharmacological activity or other direct effect in the diagnosis, cure, mitigation, treatment, or prevention of disease or to affect the structure or any function of the human body, but typically no other materials other than those used in the synthesis and/or production of such active ingredient. Accordingly, a drug substance may contain excipients used for processing or stabilizing the active ingredient, or for other reasons relating to the manufacture, processing, and/or storage of the active ingredient.

As used herein, drug product means all of the materials in the finished dosage form, including the drug substance. The drug product can be provided as a unit dosage form. A unit dosage form is the form of the drug product that is used by the patient. The unit dosage may be, for example, in various embodiments described herein a tablet, capsule, sachet, stickpack, suspension or solution. A unit dose can be administered to a patient in a single administration, and multiple unit doses may be administered to a patient in a single administration.

In many embodiments a unit dose of ALV003 will be a unit dose of ALV001*, a unit dose of ALV002, and a unit dose of additional excipients. In some embodiments, the ALV001* and the ALV002 will be combined in a single, admixed unit dose. In any of these embodiments, the combined enzyme weight ranges of the unit dose(s) administered in a single administration will be from about 100 mg to about 6 g., with the specific activities generally in the ranges set forth herein. A unit dose of ALV003 drug product therefore comprises all ingredients of the drug product, and will typically include sweeteners, flavorings, and/or excipients, as described herein, in addition to the enzymes.

A unit dosage form of ALV003 drug product can thus be formulated into two or more separate components, each of which may be viewed as a unit dose of the materials it contains. For example, excipients that may be detrimental to enzyme stability can be conveniently formulated into a component separate from either or both enzymes. The component comprising excipients detrimental to enzyme stability may sometimes be referred to as a flavor pack or a unit dose of flavor/excipients. As noted above, the enzyme component (the enzyme unit dose(s)) may be provided as one or two components, where ALV001* (or ALV001, if the proenzyme form is administered) can be admixed with or separate from ALV002.

The term "unit dose" or "unit dosage form" may also be used to reference the quantity of each enzyme or excipient in a dosage form that is administered to a patient, such that a "unit dose of ALV001*" refers to the quantity of ALV001* present in the ALV003 unit dose; and a "unit dose of ALV002" refers to the quantity of ALV002 present in the ALV003 unit dose. The unit dose for one or both enzyme components will also typically further comprise excipients, e.g. excipients that provide for enhanced enzyme stability, although some excipients, or some portion of them, may be present in a separate component. For example, the enzyme component(s) may be free of excipients such as potassium salts, cysteine, or flavoring. Any cysteine, flavoring, and/or potassium salts in the ALV003 unit dose may be administered in a separate flavor/excipient unit dose.

All components of the ALV003 unit dose may be admixed at ingestion, for example by dissolution into a potable beverage, which resulting solution is also a liquid unit dose of ALV003. For example, a unit dose of ALV003 may be dissolved or suspended in a volume of liquid of at least about 50 ml and not more than about 500 ml, e.g. at around 100 ml, 200 ml, 300 ml, or 400 ml.

The terms "celiac sprue" and "celiac disease" are used interchangeably herein and refer to an autoimmune disease of the small intestine caused by the ingestion of gluten proteins from widely prevalent food sources such as wheat. The terms, as used herein, specifically include clinically silent celiac disease, characterized by absence of gastrointestinal symptoms, and moderate to severe symptomatic celiac disease, characterized by gastrointestinal symptoms that can range from mild to severe. "Celiac disease" as used herein also includes dermatitis herpetiformis (DH), although a celiac disease patient may have none of the skin lesions associated with DH.

The term "deleterious effect of gluten ingestion" is used herein to refer to any and all undesired effects of gluten ingestion in a subject, including, without limitation, symptoms and deleterious effects resulting from T lymphocyte-driven immune response in the intestine of celiac disease patients, including gastrointestinal symptoms, such as gluten-induced small intestinal mucosal inflammation and symptoms, or even psychological distress caused by a perception that gluten causes harm to the patient. The term "deleterious effect of gluten ingestion" also includes any undesired effects of gluten ingestion on the skin of a subject, including, without limitation, symptoms characteristic of dermatitis herpetiformis.

A chromogenic assay can be used to measure enzyme activity. For ALV001* activity measurement by a suitable chromogenic assay, ALV001* samples are diluted into a volume of 50 µL of dilution buffer (100 mM Tris, 3.5 mM EDTA, 2 mM β-mercaptoethanol, 15% w/v sucrose, 5 mg/mL bovine serum albumin, pH 8.0) to a concentration of 400 nM. This volume is added to 100 µL of 1M sodium acetate buffer (pH 4.5), and incubated at 30° C. to allow for enzyme activation. After exactly 30 min., the entire volume is added to a cuvette containing 850 µL substrate (Z-Phe-Arg-pNA) solution in 5% (v/v) DMSO/$H_2O$ (50 µM substrate concentration in final assay volume). The reaction is immediately followed by monitoring A410 at 25° C. with a UV/Vis spectrophotometer. The reaction rate is measured from the initial slope of the A410 versus time, and converted to activity units using extinction coefficient of 8,800 $M^{-1}$ $cm^{-1}$ for pNA. One unit is defined as the amount of ALV001* required to release 1 µM pNA per minute in above reaction conditions.

Similarly for ALV002 activity measurement via a chromogenic assay, ALV002 samples are diluted into a volume of 100 µL of dilution buffer (100 mM Tris, 3.5 mM EDTA, 2 mM 1-thioglycerol, 2.5% w/v mannitol, 5 mg/mL bovine serum albumin, pH 8.5) to a concentration of 100 nM. This entire volume is added to a cuvette containing 900 µL substrate (Z-Gly-Pro-pNA) solution in 2.8% (v/v) DMSO/$H_2O$ and 22.2 mM sodium phosphate, pH 7.0 (50 µM substrate concentration in final assay volume). The reaction is immediately followed by monitoring A410 at 25° C. with a UV/Vis spectrophotometer. The reaction rate is measured from the initial slope of the A410 versus time, and converted to activity units using extinction coefficient of 8,800 $M^{-1}$ $cm^{-1}$ for pNA. One unit is defined as the amount of ALV002 required to release 1 µM pNA per minute in above reaction conditions.

Gluten has a high proline and glutamine content. This makes it resistant to proteolysis by gastric, pancreatic, and intestinal brush border endo- and exoproteases, which have poor specificity for peptide bonds adjacent to proline and glutamine residues. As a consequence of the incomplete gastrointestinal proteolysis of gluten, long oligopeptides (such as the 33-mer and 26-mer peptide fragments described in U.S. Pat. No. 7,303,871) accumulate in the small intestine of mammals following ingestion of gluten. Following deamidation by tissue transglutaminase in the intestine, these peptides stimulate an immune response in the intestine of celiac disease patients resulting in structural changes to the lining of the small intestine. Following the seminal work by Khosla et al. described in PCT Pat. Pub. No. 2003/068170, a number of scientific journal publications have reported the potential for proline- and glutamine-specific endoproteases, referred to as glutenases, as therapeutic agents for celiac disease because of their ability to digest these proteolytically resistant gluten epitopes.

ALV003 is a mixture of two glutenases. The two glutenases that are comprised in ALV003 demonstrate complementary substrate sequence and chain length specificity. If ALV003 comprises the proenzyme form of EPB2, ALV001, upon activation in an acidic environment (as in the stomach)

to form ALV001*, proteolyzes gluten at specific glutamine residues and reduces the amount of peptides that are immunostimulatory to T cells derived from celiac disease patients. Although ALV002 alone has relatively weak activity on intact gluten proteins, it proteolyzes the peptidic products of ALV001 digestion by cleaving at proline residues. By virtue of their complementary sequence specificity and chain length tolerance for peptides, together ALV001/ALV001* and ALV002 degrade gluten more rapidly and thoroughly than either individual enzyme alone (Gass, Bethune et al. 2007).

The complementary substrate sequence and chain length specificity described above have been demonstrated in vitro and in vivo. ALV003 proteolyzes various forms of gluten (purified gliadin, uncooked gluten flour, and whole wheat bread gluten) in vitro and eliminates >90% of immunoreactive epitopes present. In addition, ALV003 proteolyzed both gluten flour and wheat bread in the stomach of a rat in an in vivo model of gluten digestion. As noted above, at pH values typical of a postprandial stomach (3.5-5), ALV001 activates to its mature form ALV001*, which is active and stable over this pH range. ALV002 contributes to gluten digestion above pH 4. Therefore, ALV003 is active in the stomach during and following a meal. In addition, ALV003 is rapidly proteolyzed by pepsin in both simulated and fasting human gastric fluid (pH 1.8) and also by pancreatin at near neutral pH, providing a mechanism for ALV003 clearance. When incubated in human gastric samples obtained from subjects who had ingested soy milk ex vivo, ALV003 degraded gluten immunoreactive epitopes measured within 30 minutes in a dose-dependent fashion. In vitro, concentrations of ALV003 from 0.25-2.0 mg/mL were able to eliminate >90% of immunoreactive gluten peptides from 0.5-12 mg/mL gluten within 60 min.

Notable favorable properties of ALV003 include its high specificity for gluten and suitability for convenient oral dosing.

Although the following description refers to "ALV001", in some embodiments of the pharmaceutical formulations and unit dosage forms of the invention the activated form of ALV001, ALV001*, is used instead of, or in addition to, the inactive zymogen. The following description equally applies to pharmaceutical compositions comprising ALV001 and/or ALV001*.

In various embodiments of the pharmaceutical compositions of the invention, a reducing agent is included to enhance stability. For example, the reducing agents sodium metabisulfite (MBS) and cysteine have been shown to maintain ALV001 activity in food and human gastric fluid using four independent assays, chromogenic activity, T cell assay, mass spectrometry, and ELISA, which were used to quantify the stability and activity of ALV001 in the presence of a complex meal. Results showed that cysteine (100 mg per meal, i.e., 100 mg per dose of ALV001*), helps to stabilize ALV001* activity in meals containing specific food items while MBS helps stabilize ALV001* activity in human gastric fluid. Both cysteine and MBS are able to enhance ALV001 activity even in the absence of human gastric fluid or oxidizing food items suggesting that these agents enhance enzyme activity as well as stability. One hundred milligrams of cysteine per meal were utilized to achieve maximal ALV001 stability under the test conditions employed. Mechanistically, MBS and cysteine are included in certain pharmaceutical compositions of the invention to counter the oxidative effects on ALV001 that derived from the food and gastric contents. Pharmaceutical formulations of ALV001 (ALV001*) and ALV003 of the invention may therefore contain cysteine (e.g., about 100 mg, although more or less cysteine may be employed, depending on the amount of ALV001 in the dosage form) or MBS (e.g., about 8 mg although more or less MBS may be employed, depending on the amount of enzyme in the dosage form), or both cysteine and MBS.

A dosage form of the invention may, for example and without limitation, contain 100 mg to 2 g ALV003 (e.g., 50 mg of each of ALV001 (or corresponding amount of ALV001*) and ALV002 to 1000 mg each of ALV001 (or corresponding amount of ALV001*) and ALV002), in powder or optionally in a tablet form, optionally with added citric acid, sodium citrate, metabisulfite, and/or cysteine. The dosage form may contain a lyophilized powder of ALV001 (or ALV001*) in which sodium metabisulfite had been added to the solution prior to lyophilization at a ratio from 50:8 (w/w ALV001:MBS) to a ratio of 3000:4 (w/w).

A dosage form may also contain a spray dried powder of ALV001 (or ALV001*) in which sodium metabisulfite had been added to the solution prior to spray drying at a ratio from 50:8 (w/w) to a ratio of 900:4 (w/w).

In another embodiment, a dosage form may contain ALV001 (or ALV001*) in a range of 50 to 1000 mg, e.g. 100 to 900 mg, and sodium metabisulfite in a range of 1 to 100 mg, e.g., 5 to 25 mg, or 1 to 10 mg. If ALV001* is used instead of ALV001, the amounts given are by weight of the corresponding amount of ALV001 (this convention is used for all weights of ALV001* herein).

Another dosage form may contain pulsed release ALV001 (or ALV002 or both or ALV001* or both ALV001* and ALV002) in a range of 50 to 2000 mg, where about half of the dose is immediately released upon ingestion and the remainder is released in a second pulse 20 minutes to 1 hour after ingestion.

In other embodiments, a dosage form may contain a protease (ALV001 or ALV001* or ALV002 or both ALV002 and one of ALV001 or ALV001*) and a quantity of an antioxidant that achieves an antioxidant concentration of at least 30, 50, 100, or 200 µM in the stomach.

In further embodiments, the dosage form contains ALV001 (or ALV001*) and/or ALV002 and a quantity of a compound that generates a concentration of free thiol of at least 100, 200, or 500 µM in the stomach.

In further embodiments, the dosage form contains both ALV001 (or ALV001*) and ALV002 where one or both enzymes are formulated to provide an immediate release and the other enzyme or remainder of both enzymes is released either in a pulsed release or a controlled release.

As is apparent from the foregoing, all of the ALV001 (and ALV001*) dosage forms above can also be modified to include a second protease, such as a prolyl endopeptidase (PEP). In one embodiment, the PEP is *Sphingomonas capsulata* PEP, for example and without limitation, as described in PCT Pub. No. 2008/115411, which is referred to herein as ALV002. In various embodiments, between 1-2000 mg of the PEP and ALV001 (or ALV-001*) are dosed at a PEP:ALV001 weight ratio of between 1:100 to 100:1, more preferably between 1:20 to 20:1, more preferably between 1:5 and 5:1, and most preferably at a 1:1 w/w ratio. In one embodiment, the dosage form is constructed so that the ALV001 (or ALV-001*) and antioxidant, e.g., sodium metabisulfite, are immediately released, and the PEP is released either immediately; or is released in one or more short, delayed pulses (from 10 minutes to 2 hours); or is released in sustained release over 10 minutes to 2 hours. In the ALV003 dosage forms (which collectively refers to the separate dosage forms of ALV-001 or ALV-001* and ALV- 002 and the flavor/excipient dose form), the antioxidant may be an antioxidant other than or in addition to sodium metabisulfite. Thus, the additional or other antioxidant may, for example, be selected from the group consisting of sodium sulfite, sodium bisulfite, potassium bisulfate, potassium metabisulfite, alone or combination; sodium thiosulfate; glutathione, cysteine, homocysteine, sodium dithionite, thioglycerol; and acetylcysteine.

The compositions herein may, for example, be in the form of powdered drug substance, roller compacted granules, or pellets of the enzyme. The antioxidant may be either contained in the granules or pellets or blended with the granules or pellets and either filled or compressed into a dosage form. The antioxidant may also be included in separate package, layer, or coated granules/pellets, as described previously.

In general, the pharmaceutical formulations used in accordance with the present invention can be in the form of, for example and without limitation, particles, particles in capsule or sachet, stickpack, or tablet. Tablets may be single layer, bilayer, or multilayer or may be core tablets with enclosing compressed shells or layers and any of these tablets may be coated or uncoated. The formulation can, for example and without limitation, be added to a food or drink and then administered, for example, as a sprinkled powder or granule formulation or as a spread in the form of a jam or powder. A capsule of low water content may be desired for stability, and hypromellose capsules, HPMC, of size 1, 0, or 00, can be used. Capsules can be packaged in a dry environment either with desiccant or desiccant packs or if in blisters under dry nitrogen or other dry environment.

The pharmaceutical formulations used in accordance with the present invention can comprise a lubricant such as magnesium stearate, stearic acid, sodium stearyl fumarate, or sodium stearyl lactylate, hydrogenated vegetable oil (such as hydrogenated and refined triglycerides of stearic and palmitic acids). These may be at 0.1 to 5% of weight of the dosage form. If mannitol is contained at a high concentration in the lyophilized powder, then higher concentrations of lubricant may be used.

The protease powder may be blended with lubricant or other excipients such as a filler or binder and granulated. If the protease is unstable with water and temperature, then these can be roller compacted into granules, if necessary using chilled rollers for stability. One may optionally include an agent that modifies or controls pH, at least for the first few minutes after the dosage form is in the GI tract, to facilitate activation of zymogen proteins such as ALV001.

Fillers such as dicalcium phosphate, microcrystalline cellulose, maltodextrins, mannitol, lactose, sucrose, pregelatinized starch, or trehalose may be included and blended with the powders or included in the lyophilized powder or spray-dried powder to prepare a pharmaceutical formulation of the invention. More hydrophilic fillers such as microcrystalline cellulose may be avoided for certain enzymes, such as ALV001.

Superdisintegrants such as crospovidone, sodium starch glycholate, or sodium croscarmellose may be added to prepare a pharmaceutical formulation of the invention.

Controlled-release excipients may be blended in to form polymeric drug-containing matrices. These matrices may be from about 1 mm in diameter to the size of a full tablet 6 to 12 mm in width and even 1.8 cm or more in length. These matrices can provide extended-release into the stomach being retained with food for 20 minutes to several hours depending on the size. These matrices may or may not be swellable. If swellable, extended-release hydrophilic polymers that are appropriate include cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, polyvinyl alcohol), xanthan gum, maleic anhydride copolymers, polyvinyl pyrrolidone), starch and starch-based polymers, poly (2-ethyl-2-oxazoline), poly(ethyleneimine), polyurethane hydrogels, methacrylate copolymers, and crosslinked polyacrylic acids and their derivatives. Further examples are copolymers of the polymers listed in the preceding sentence, including block copolymers and grafted polymers. Extended-release coatings could also be prepared on these particles using some of the above polymers.

In one embodiment, the pharmaceutical composition is a powder. In this embodiment, the powdered forms of ALV001 (or ALV-001*) and ALV002 may be separately packaged, in sachets or stickpacks for example, and contemporaneously administered to the patient, or the powdered forms of the two proteases may be admixed prior to administration. Where powders are employed, the powders are typically dissolved or suspended in a potable liquid that is then drunk by the patient.

In one embodiment, the pharmaceutical composition is a powder formulation of ALV001 (or ALV-001*) that can be prepared in a unit dose form containing from about 50 mg to about 1500 mg, e.g. 450 mg, of ALV001 (or ALV-001*, typically ≥5000 proteolytic activity Units/mg protein, i.e., 7300 to 7500 Units/mg, but the specific activity can be lower, i.e., about 2500 Units or even lower, depending on a variety of factors, such as the patient and the intended application) with any of the excipients described herein, including but not limited to those shown in the table below.

In one embodiment, the pharmaceutical composition is a powder formulation of ALV002 that can be prepared in a unit dose form containing 50 mg to about 1500 mg, e.g. 450 mg, of ALV002 (typically ≥3000 proteolytic activity Units/mg protein, i.e., 6200-7000 Units/mg protein, but the specific activity can be lower, i.e., about 1500 Units or even lower, depending on a variety of factors, such as the patient and the intended application) with any of the excipients described herein, including but not limited to those shown in the tables below.

Advances provided by the formulations of the invention include a citrate buffering system that ensures that the liquid dosage form ingested by the patient will have a pH in the range of 4 to about 6 and to promote that the pH of the patient's stomach contents remains in this range for a period of from about 5 to at least about 30 or more minutes after ingestion of the liquid dosage form. In some embodiments the pH is maintained in a range of about 4.5 to about 5.5. Conveniently, formulations can be tested for buffering capacity in an in vitro model, as described in the examples below.

When a buffering system containing sodium is employed, the amount of buffer needed to ensure this pH range is maintained for the desired period of time can result in a high sodium dose, which can be undesirable for certain patients. Thus, in some embodiments, the invention provides for the use of potassium salts, in place of some or all of the sodium salts, to avoid this problem. However, certain potassium salts can unfavorably affect stability of activity of the enzymes during storage, and it is therefore desirable to provide such potassium salts in a separate flavor pack or other dose form that keeps it separated from the enzymes.

As used herein, "buffer" refers to a mixture of either a weak acid and its conjugate base or a weak base and its conjugate acid that, when in solution, resists changes in pH.

In some embodiments the buffer system is a citrate buffer system, and the total dose of citrate buffer in a unit dose formulation is at least about 500 mg, at least about 750 mg, at least about 1000 mg, and not more than about 5000 mg, not more than about 4000 mg, not more than about 3750 mg. It will be understood by one of skill in the art that the relative proportions of citrate and citric acid are adjusted to achieve the desired pH.

As used herein "citrate buffering system" refers to a combination of citric acid and either sodium citrate or potassium citrate or both sodium citrate and potassium citrate. Those of skill in the art will recognize that various hydrates and salts of citrate are available and can adjust the amounts accordingly based on the information provided herein. Generally, however, and for most pharmaceutically acceptable salts and hydrates of citrate, to achieve the desired buffering, each dose of ALV003 will contain at least 300 mg of the citrate buffering system, often at least 500 mg of the citrate buffering system, often at least a gram of the citrate buffering system, sometimes at least 2 g of the citrate buffering system, and sometimes as much as at least 3 g of the citrate buffering system. In various embodiments, only a limited amount of sodium citrate, such as at least 250 mg, such as at least 400 mg but no more than a g or 0.5 g or sodium citrate will be employed per ALV003 dose. In these embodiments, potassium citrate is employed in amounts ranging from at least 500 mg to at least 2 g per dose. In all embodiments, citric acid is employed in amounts ranging from at least 250 mg to about 1 g per dose.

In some embodiments, citric acid is provided at an admixed unit dose (i.e. the combined dose of enzymes and flavor pack) of at least about 20, at least about 50 mg, at least about 75 mg, at least about 100 mg, at least about 200 mg, at least about 300 mg; and not more than about 1500 mg, not more than about 1250 mg, not more than about 1000 mg, not more than about 750 mg. The dose of citric acid can be divided between the flavor pack and the enzymes contained in the ALV003 formulation. Where ALV001 and ALV002 are separated, and a separate flavor pack is employed, the dose of citric acid can be divided between each of the enzymes and the flavor pack. In various embodiments, the pH of the buffer systems in all packs or dosage form components is comparable so that the pH of the resulting drink will be similar independent of order of addition.

In some embodiments, the total dose of citrate (combining sodium and potassium salts) is at least about 1000 mg/unit dose, at least about 1200 mg/unit dose, at least about 1500/unit dose and not more than about 3500 mg/unit dose, not more than about 3000 mg/unit dose, not more than about 2750 mg/unit dose. Potassium citrate is preferably substantially provided in a flavor pack and is not included in the enzyme formulation. Potassium citrate may be present in at least about 500 mg/unit dose, at least about 750 mg/unit dose, and not more than about 2500 mg/unit dose, not more than about 2000 mg/unit dose. The balance can be provided as sodium citrate, e.g. in a unit dose of at least about 500 mg, at least about 750 mg/unit dose, and not more than about 1500 mg/unit dose, not more than about 1250 mg/unit dose, not more than about 1000 mg/unit dose.

Advances provided by the formulations of the invention also include a separately formulated flavor pack. Hygroscopic materials, including potassium salts, cysteine, and flavoring agents can unfavorably affect stability and activity of the ALV003 enzymes. Thus, in various embodiments of the drug products of the invention, any hygroscopic excipients are packaged separately or isolated from the two enzymes in the ALV003 drug product. Certain sweeteners can adversely affect ALV002 stability. Thus, in some embodiments, the ALV003 drug product has a sweetener other than acesulfame K or saccharin. In some embodiments, the ALV003 has a sweetener selected from the group consisting of sucralose, aspartame, and neotame. In some embodiments, the sweetener is packaged separately from the ALV001 (or ALV001*) and ALV002, e.g. in a flavor pack.

Throughout this application formulations have been specified for weights or weight ranges of specific excipients, and these weights or weight ranges are based on the specific salts and/or hydrate or solvate forms described in the examples. Other salt, solvate or hydrate forms may be substituted for those described in these examples. The appropriate weight or weight range for these substituted salts, solvates, or hydrates would be using a comparable millimolar quantity that can easily be calculated from the weight or weight range of the salt or hydrate described in the example.

The formulations of the invention also comprise an antioxidant, as disclosed in WO 2010/021752, herein specifically incorporated by reference. In some embodiments the antioxidant is sodium metabisulfite at a concentration for the admixed unit dose (i.e. the combined dose of enzymes and flavor pack) of at least about 1 mg, at least about 2 mg, at least about 4 mg, around about 6 mg, around about 8 mg, around about 10 mg, not more than about 32 mg, not more than about 25 mg, and not more than about 20 mg. Where the enzymes are separately formulated, the sodium metabisulfite is usually provided with the ALV001 drug product.

The formulations can also comprise a chelating agent, e.g. EDTA. In some embodiments the chelating agent is EDTA at a at a concentration for the admixed unit dose (i.e. the combined dose of enzymes and flavor pack) of at least about 1 mg, at least about 2 mg, at least about 3 mg, and not more than about 100 mg, not more than about 80 mg, not more than about 75 mg, and may be around about 5 mg to about 60 mg depending on the amount of enzyme that is present. Where the enzymes are separately formulated, the EDTA can be divided between the two or provided with either.

Cysteine can be included in the flavor pack at a unit dose of at least about 25 mg, at least about 50 mg, at least about 75 mg, and not more than about 250 mg, not more than about 200 mg, not more than about 150 mg, and may be provided at around about 100 mg. In some embodiments the taste of cysteine in the flavor pack is masked. Methods of masking the taste of cysteine are known in the art (see, for example, reviews by Vummaneni and Nagpal (2012) International Journal of Research in Pharmaceutical and Biomedical Sciences ISSN: 2229-3701; Ahire et al. (2012) Pharma Science Monitor 3(3): ISSN: 0976-7908). Included are polymeric coatings, e.g. starch; povidone, gelatin, methylcellulose, ethyl cellulose, Kollicoat Smartseal 30 D methyl methacrylate, diethylaminoehylmethacrylate copolymer dispersion. etc., which provide a physical barrier. The granules or particles to be coated may be coated directly or first granulated or roller compacted and then coated. Instead of or in addition to coating, a complexing agent such as an ion exchange resin or a cyclodextrin may be used. Suspensions of coating materials and suitable excipients designed to mask the taste of cysteine may be applied to particles comprised of cysteine in a coating pan or fluid bed coater and then dried to provide a taste masking coating. An exemplary suspension for this coating includes Smartseal 30 D at 33.5%, DI water at 22%, tributyl citrate at 1.5%, and BHT at 0.1%. An example of a suitable thickness for the coating is 1.5 to 4.5 mg/cm$^2$.

Neutral methacrylate films of Eudragit PO may also be used for taste masking in accordance with the invention. Examples for producing suitable material include placing cysteine granules or roller-compacted granules of cysteine and microcrystalline cellulose (or maltodextrin) from 1:1 to 3:1 in a fluid bed coater. The aminomethacrylate copolymer NF, polyethylene glycol (or acetyl tributyl citrate or triethyl citrate) as plasticizer, a pore-forming agent, such as talc, and colloidal silicon dioxide (antistatic and flow) are sprayed on as a coating. The coated granules, pellets, or beads are dried at 50° C. or above. An additional curing step may be used. A rapidly dissolving sub-coat may be used if desired. The granules, beads, or pellets are placed in a fluid bed, and a suspension of hypromellose with colloidal silicon dioxide is sprayed on as sub-coating from an aqueous ethanol solution. An alternative suitable method involves spraying the particles comprising cysteine with a suspension of Eudragit E100:Hypromellose (3:1 to 5:1) with colloidal silicon dioxide from aqueous ethanol solution and then drying the coated particles. An antistatic coating of colloidal silicon dioxide may be applied from an ethanolic solution as an additional optional step. Drying is to be done between 35 and 55 C.

Other examples of coating suspensions that can be used for taste masking the cysteine are Surelease (ethylcellulose) and Opadry (HPMC) in a 80:20 ratio at 15% to 205% weight gain on the uncoated cys granules. If dissolution of the coated cysteine particles is too slow, a superdisintegrant such as Na croscarmellose can be added at under 10% to speed dissolution.

When coated cysteine is used, the thickness of the coating needs to be such that it effectively prevents dissolution prior to ingestion but rapidly disintegrates after ingestion. In those formulations employing a taste-masked cysteine, the amount of sweetener and/or flavor can be reduced relative to any of the embodiments described herein, e.g. reductions of 2-fold, 3-fold, 4-fold, or 5-fold, in either the sweetener or the flavoring, or both, are suitable for those formulations and unit dose forms employing masked cysteine.

The protein (ALV001/ALV001* and ALV002) content of the compositions may vary within a wide range, such as, for example, between about 10% and about 85%, or between about 20% and about 75%, wherein ALV001/ALV001* and ALV002 may be present in equal or different percentage amounts but are often present in identical or substantially similar amounts. In one embodiment, the compositions contain about 20% ALV001 and about 30% ALV002. In another embodiment, the compositions contain about 40% to 85% of each of ALV001* and ALV002.

Prior drug product compositions for ALV001 and ALV002 used in clinical testing include the following (referred to as "Clinical Product"):

TABLE 1

ALV001 Drug Product

| Component | Quantity per dose/bottle |
| --- | --- |
| ALV001 (EP-B2) | 450.0 mg ± 30.0 mg |
| EDTA | 69.9 mg ± 14.1 mg |
| Mannitol | 879.0 mg ± 175.8 mg |
| Monothioglycerol | 8.4 mg ± 1.8 mg |
| NaCl | 10.8 mg ± 8.1 mg |
| Sucrose | 351.6 mg ± 70.2 mg |
| TRIS | 508.2 mg ± 101.7 mg |
| Citric Acid Anhydrous | 450.0 mg ± 25.0 mg |

TABLE 1-continued

ALV001 Drug Product

| Component | Quantity per dose/bottle |
| --- | --- |
| Sodium Metabisulfite | 8.0 mg ± 1.0 mg |
| Cysteine Hydrochloride Monohydrate | 100.0 mg ± 10.0 mg |

TABLE 2

ALV002 Drug Product

| Component | Quantity per dose/bottle |
| --- | --- |
| ALV002 (PEP) | 450.0 mg ± 30.0 mg |
| EDTA | 32.7 mg ± 6.6 mg |
| Mannitol | 439.5 mg ± 87.9 mg |
| Monothioglycerol | 3.9 mg ± 0.9 mg |
| Sodium Phosphate | 10.8 mg ± 2.1 mg |
| TRIS | 238.2 mg ± 47.7 mg |
| Calcium Carbonate | 400.0 mg ± 25.0 mg |

The present invention arose in part from the discovery that adjustment of excipient amounts to provide increased buffering capacity improved performance. The amount of sodium citrate added to provide this increased buffering capacity results in high sodium levels such that, in various embodiments, a portion of the citrate is provided in the form of potassium citrate. Potassium citrate absorbs water, which may decrease stability of the ALV001* and/or ALV002; in some embodiments all or a significant portion of any of the potassium citrate in the ALV003 drug product is packaged separately from the ALV001 (or ALV001*) and ALV002. Similarly, the cysteine in the ALV003 drug product can absorb water, and in some embodiments all or a significant portion of the cysteine in the ALV003 drug product is packaged separately from the ALV001 (or ALV001*) and ALV002.

The present invention also arose in part from the discovery that inclusion of the sweeteners acesulfame K and saccharin in the ALV003 drug product had a deleterious effect on ALV002 stability. Thus, in some embodiments, the ALV003 drug product has a sweetener other than acesulfame K or saccharin. In some embodiments, the ALV003 has a sweetener selected from the group consisting of sucralose, aspartame, and neotame. In some embodiments, the sweetener is packaged separately from the ALV001 (or ALV001*) and ALV002.

Optionally, the formulations may contain a flavor agent(s), which may be present in the ALV001* and/or ALV002 formulation or may be separately packaged. When the formulation is prepared in the form of separate drug products, in one particular embodiment, the ALV001* and ALV002 drug products do not contain any flavor agent; rather, the favor agent(s) is present in an additional product, which may optionally contain one or more sweeteners, fillers, excipients, or buffers. The additional fillers, excipients, and/or buffers can include materials that are deleterious to the stability/activity of either enzyme, such as potassium citrate and cysteine, which may absorb water and decrease stability of any enzyme in contact therewith.

A formulation for the flavoring with a range of buffer amounts is adjusted for use with different flavors and volumes of liquid for reconstitution and drinking, i.e., 10 to 300 ml, more typically 50 to 250 ml, and often 100 to 240 ml. The amounts of buffer (0.1 to 5 g), sweetener (20 to 200 mg for sucralose), and flavoring (100 to 700 mg) may all be varied over a wide range for different desired volumes of the drink to optimize the flavor, and in consideration of cysteine taste masking. Any pharmaceutical or food flavoring may be selected provided it does not adversely affect the activities of the enzymes. Typical flavors are grape, orange, lime, lemon, lemon-lime, fruit punch and among the preferred flavors are watermelon, pomegranate, caramel, pineapple, mango, peach, and pumpkin spice.

Reconstitution of a powdered form of the drug product may take place using a potable liquid, such as, for example, cold or room temperature water or fruit juice. In one embodiment, the formulations listed in the table immediately above are reconstituted in about 200 mL of cold or tepid (about room temperature) water.

In various embodiments, the drug product formulations are packaged separately. For example, the ALV001 (or ALV001*) and ALV002 may be in separate dose forms. Similarly, the flavoring and certain buffers or other excipients may be in a separate dose form. In various embodiments the two enzymes, and the flavoring, are in separate stickpack dose forms. These stickpacks are, in some embodiments, connected with a heat seal or other attachment between them. The contents of the two or more attached stickpacks are emptied into the fluid for dissolution or suspension and drinking. For the case where the stickpacks have a burstable user-activated seal between them, the seal is intact during storage, burst by the user, and then the contents of the stickpacks emptied (or mixed and emptied) into the liquid simultaneously. The user activated, burstable seal can be made with a lower seal strength than the packaging heat seal by a combination of seal width, heat seal die dwell time during sealing, and heat seal die temperature during sealing. The stickpack may have a registration mark for alignment to provide these separate seals or the sealing may be done during a single sealing process.

Suitable ALV001 (or ALV001*) and ALV002 placebos contain the same ingredients as the corresponding formulated drug substances (and corresponding drug products), except for the removal of monothioglycerol and EDTA and the addition of TRIS-HCl (tris hydroxymethylaminomethane-HCl). All are free-flowing white to off-white powders. ALV001, ALV002, and matching placebos can be stored at room temperature (15 to 25° C.) or under refrigerated conditions.

It is also possible to fill the ALV001 and ALV002 powders into other types of containers, such as sachets, sprinkles, powders, and the like, to prepare drug products of the invention.

Uses of Drug Products

ALV003 and pharmaceutical compositions comprising ALV003 can be used in methods for protecting a patient from a deleterious effect of gluten ingestion. In particular, ALV003 can be used to prevent the manifestations of or treat celiac disease, including celiac sprue and/or dermatitis hepatiformis, including prevention and treatment of various symptoms or clinical manifestations of these diseases and conditions.

Clinical manifestations include, without limitation, mild gastrointestinal disturbances, chronic gastrointestinal symptoms, malabsorption, weight loss, isolated iron deficiency anemia, various manifestations outside the gut, such as osteoporosis, peripheral and central nervous system involvement, mild or severe liver disease, infertility problems, and the-gluten-induced skin disease, dermatitis herpetiformis. The gluten-induced small bowel pathology in celiac disease is characterized by an inflammatory reaction that is accompanied by villus atrophy and hypertrophy of crypts.

Symptoms of celiac disease include, without limitation, diarrhea, constipation, flatulence, abdominal pain, bloating, nausea, fatigue, skin rashes, difficulty thinking, and headache.

Patients suitable for treatment in accordance with the invention may be symptomatic or asymptomatic at the time of treatment. If the patient is symptomatic, symptoms may range from mild to moderate to severe. In a particular embodiment, moderately to severely symptomatic celiac sprue patients are treated. In another embodiment, the treatment is used in moderately to severely symptomatic celiac disease patients as an adjunct to a GFD (gluten-free diet) for the attenuation of gluten-induced small intestinal mucosal injury and symptoms. In another embodiment, the patient treated has experienced moderately to severe symptoms of celiac disease within one month from first administration.

The severity of the disease can also be determined using medical diagnostic methods known in the art, such as upper gastrointestinal endoscopies, biopsies, small intestinal mucosal morphometric analyses, determination of the villus height/crypt depth ratio to establish manifest gluten-induced mucosal architectural change, and measuring the intraepithelial densities of all CD3+ (T) lymphocytes and densities of $\alpha\beta+$ and $\delta+$ T cell receptor-bearing IELs to reveal gluten-induced inflammatory changes.

While thrice daily (TID) administration is contemplated in various embodiments of the invention (as most patients eat three meals per day and the ALV003 is taken with a meal), QD administration may also be practiced, i.e., when a patient is consuming only one gluten-containing (or potentially gluten-containing) meal per day. Thus, ALV003 may be administered when a patient is ingesting food suspected of containing, or known to contain, gluten, and the number of administrations per day is neither limited nor fixed.

Optionally, the patient's serology status may be determined prior to administration of the compositions herein. Determination of the serology status may comprise an antibody test, such as anti-gliadin antibodies (AGA), anti-reticulin antibodies (ARA), IgA anti-human tissue transglutaminase (TTG) antibodies (TG2), and IgA anti-endomysial antibodies (EMA), and anti-deamidated gliadin peptide (DGP) tests.

Administration may occur at mealtime, such as with a major meal or meals, e.g. one to three times, such as three times, per day.

A typical daily dose for oral administration of ALV003 is in the range of about 100 mg to about 3 g. As discussed above, the daily dose can be reached by one or more administrations, typically taken with food.

In various embodiments, ALV003 is administered with food containing at least 20 mg but not more than about 25 g of gluten, or no more than about 1 g of gluten, or no more than about 2 g of gluten, or no more than about 3 g of gluten, or no more than about 5 g of gluten, or no more than about 10 g of gluten.

In another embodiment, ALV003 has equal amounts of (ALV001 and/or ALV001*), and ALV002, by weight or by units of activity, including embodiments wherein ALV001/ALV-001* has a specific activity of at least 5000 or more proteolytic activity units per mg, and said ALV002 has a specific activity of at least 3000 or more proteolytic activity units per mg.

Further details of the invention will be illustrated by the following non-limiting examples.

Example 1

Buffers composed of acetate and citric acid or citrate and citric acid at pH 5.4 over a range of 0.75-3 g of total buffer were prepared. These buffers were added into a gluten-free vegetable korma test meal and titrated by adding 2 ml of 100 mM HCl followed by a pH measurement. FIG. 1 shows that addition of buffer can enhance the buffering capacity in a dose dependent manner relative to the unbuffered meal. The data indicate that the buffering capacity of acetate is about twice as much as citrate, and a 3 g citrate buffer can double the amount of HCl necessary to get the meal pH below 3.0 compared to the meal without buffer added. This example demonstrates that ALV003 dose forms containing at least 0.75 g and up to 3 g of citrate buffer at about pH 5.4 provide a significantly longer duration for the enzymes to degrade gluten effectively by maintaining the pH above 3.5 until after 2 or more millimoles of hydrochloric acid were added. Similar superior results may be achieved in accordance with the invention using similar amounts of citrate buffer at pH ranging from 5 to 5.5. As discussed above, the citrate buffer may be divided into the various solid dose forms of ALV001*, ALV002, and the other flavor/excipients in any amounts for the convenience of the manufacturer. In those embodiments where potassium citrate is employed in the citrate buffer, the potassium citrate may be contained entirely in the flavor/excipient unit dose form.

Example 2

A series of citrate buffers at either pH 5.4 or 5.2 ranging from 1-3 g of total buffer were prepared and added to a vegetable korma test meal (FIG. 2). The meal was titrated by adding 2 ml of 100 mM HCl followed by a pH measurement. These citrate buffers were compared to a formulation used in a previous clinical trial and a formulation without buffer added. The 2 g citrate buffers at either pH 5.4 or 5.2 were able to buffer the meal similarly to the clinical trial formulation and increased the amount of HCl necessary to reduce the pH to 3.0 by approximately 50% compared to the unbuffered meal. This example demonstrates that ALV003 dose forms containing at least 2 g of citrate buffer at pH 5.2-5.4 provide a substantially longer period of time at a favorable pH for the enzymes to effectively degrade gluten by maintaining the pH above 3.5 until 2 or more millimoles of hydrochloric acid were added. Similar superior results may be achieved in accordance with the invention using similar amounts of citrate buffer at pH ranging from 5 to 5.5. As discussed above, the citrate buffer may be divided into the various solid dose forms of ALV001*, ALV002, and the other flavor/excipients in any amounts for the convenience of the manufacturer. In those embodiments where potassium citrate is employed in the citrate buffer, the potassium citrate may be contained entirely in the flavor/excipient unit dose form.

Example 3

A series of citrate buffers at either pH 5.4 or 5.2 ranging from 1-3 g of total buffer were prepared and added to a water test meal to simulate a worst-case scenario of a low buffering meal (FIG. 3). The water meal was titrated by adding 2 ml of 100 mM HCl followed by a pH measurement. These citrate buffers were compared to a formulation used in a previous clinical trial and a formulation without buffer added. Addition of buffers significantly enhanced the buffering capacity relative to water without buffer. This example demonstrates that ALV003 dose forms containing at least 1 g and up to 3 g of citrate buffer at pH 5.4 provide superior results by maintaining the pH above about 4 until about 0.5 millimoles or more of hydrochloric acid were added. Similar superior results may be achieved in accordance with the invention using similar amounts of citrate buffer at pH ranging from 5 to 5.5. As discussed above, the citrate buffer may be divided into the various solid dose forms of ALV001*, ALV002, and the other flavor/excipients in any amounts for the convenience of the manufacturer. In those embodiments where potassium citrate is employed in the citrate buffer, the potassium citrate may be contained entirely in the flavor/excipient unit dose form.

Example 4 Sweetener Test

Figure 4B:
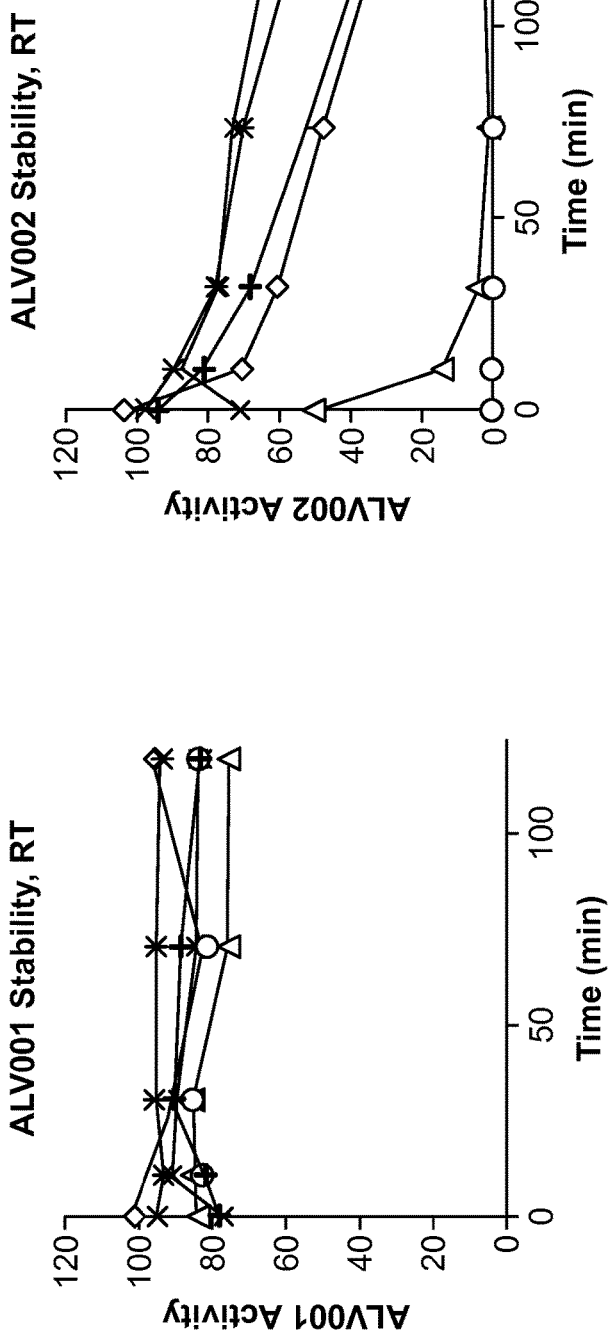
FIGS. 4A-4B. Stability of ALV001 and ALV002 in solutions containing 1% artificial sweetener, including acesulfame potassium, aspartame, neotame, saccharin, and sucralose.
Figure 4A:
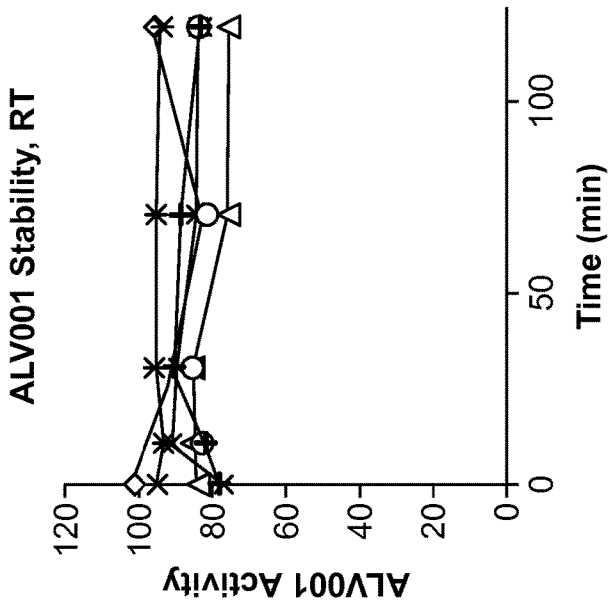

The stability of ALV001 and ALV002 in solutions containing 1% (all percentages in this example are w/v) artificial sweetener, including acesulfame potassium, aspartame, neotame, saccharin, and sucralose, was tested by reconstituting enzyme powder in buffered formulations containing these sweeteners at room temperature and measuring chromogenic enzyme activity over time (FIGS. 4A and 4B). None of the sweeteners impacted ALV001 stability with complete stability observed over the course of the study (FIG. 4A). However, acesulfame potassium and saccharin resulted in a more rapid decrease in ALV002 activity than control samples (FIG. 4B). The ALV002 sample dissolved in 1% saccharin resulted in heavy precipitation and the ALV002 sample dissolved in acesulfame potassium resulted in a turbid solution.

The stability of ALV001 and ALV002 in solutions containing artificial sweeteners, including 0.25% acesulfame potassium, 0.25% aspartame, 0.01% neotame, 0.25% saccharin, and 0.25% sucralose, was tested by reconstituting enzyme powder in formulations containing these sugars at room temperature and measuring chromogenic enzyme activity over time (FIGS. 5A and 5B). None of the sweeteners impacted ALV001 stability with complete stability observed over the course of the study (FIG. 5A). However, 0.25% acesulfame potassium and 0.25% saccharin resulted in a more rapid decrease in ALV002 activity than control samples (FIG. 5B). While addition of even 0.25% of saccharin or acesulfame potassium decreased ALV002 enzyme activity substantially and rapidly, surprisingly addition of as much as 1% sucralose, aspartame, or neotame did not significantly impact ALV001 or ALV002 activity. Only certain sweeteners may be used and still maintain ALV002 activity. The sweetener may be included in enzyme stick-packs or may be included in the flavor pack.

Example 5 Formulation Comparison

The following 4 dosage forms for ALV001 were prepared and tested in vitro: 1) fast dissolving tablets, 2) slow dissolving tablets, 3) granules that were dissolved in liquid prior to use (liquid formulation), and 4) the same granules that were sprinkled on the meal (sprinkles). All 4 dosage forms used the same granules. For this study, drug substance of the proenzyme (ALV001 at about 22% protein content w/w) was used.

For all 4 dosage forms, roller compacted granules for 123 unit dosage forms (each 50 mg protein) of ALV001 drug substance (22% protein content w/w) were prepared as follows:

TABLE 3

| Ingredient | Grade | Supplier | Quantity per Unit (mg) | Quantity for 123 units (g) |
|---|---|---|---|---|
| Intragranular Composition | | | | |
| ALV001 (Protein Content: 22%) | N/A | Alvine | 227.30 | 27.958 |
| Sucrose | NF | Fisher | 121.91 | 14.994 |
| Sodium stearyl fumarate | NF | JRS Pharma | 7.22 | 0.888 |
| Sodium metabisulfite | NF | Spectrum | 2.67 | 0.328 |
| Citric acid anhydrous | USP | J T Baker | 119.99 | 14.759 |
| Cysteine Monohydrochloride Monohydrate (L-Cysteine) | FCC | Spectrum | 33.00 | 4.059 |
| Total | | | 512.09 | 62.986 |

The ingredients were blended and mixed by hand in a polyethylene bag for 10 minutes. All sieving, weighing, and blending operations were done between 10 and 15% relative humidity (RH).

The powder blend was transferred to a TFC-LAB Micro Roller Compactor/Granulator, and these operations were performed between 30 and 35% RH. The process parameters for the roller compactor were as follows:

TABLE 4

| Parameter | Details |
|---|---|
| Roller Spec. | 50 mm dia. × 24 mm W |
| Roller Speed | 2.0 RPM |
| Roller Ammeter | 0.0-0.4 |
| Screw Speed | 15.0 RPM |
| Screw Ammeter | 0.0-0.4 |
| Roller Pressure | 1-2 tons (@400-850 psi) |
| Process Time compaction | Variable |

The roller compacted sheets were screened through the granulator with a sieve with #20 mesh and a granulator rotor speed of 4300 rpm. The calculated yield was 95.51%.

Granules were stored in polypropylene bottles with desiccant (Sorb-It, 1 g canister) at 2 to 8° C.

All handling during the preparation of the dosage form was done under low relative humidity conditions between 10 and 15% RH. To prepare the tablets, the granules were weighed and blended in a polyethylene bag by hand for 10 minutes with the extragranular powders listed in the tables below.

TABLE 5

| | | Slow Dissolving Tablet | | |
|---|---|---|---|---|
| Ingredient | Grade | Supplier | Quantity per Unit (mg) | Quantity for 71 units (g) |
| ALV001 Granules | N/A | N/A | 512.08 | 36.358 |
| Sodium stearyl fumarate | NF | JRS Pharma | 3.97 | 0.282 |
| Total | | | 516.05 | 36.640 |

TABLE 6

| | | Fast Dissolving Tablet | | |
|---|---|---|---|---|
| Ingredient | Grade | Supplier | Quantity per Unit (mg) | Quantity for 52 units (g) |
| ALV001 Granules | N/A | N/A | 512.08 | 26.628 |
| Sodium stearyl fumarate | NF | JRS Pharma | 3.97 | 0.206 |
| Sodium bicarbonate | USP | J T Baker | 60.00 | 3.120 |
| Total | | | 576.05 | 29.954 |

The tablets were compressed on a tablet press manually with B tooling. For this compression step, 30 to 40% RH was maintained.

The physical properties of the tablets are summarized below:

TABLE 7

| Tablet | Hardness (kp) | Thickness (mm) | Weight (mg) |
|---|---|---|---|
| Slow Release | 5.0 | 5.48 | 512.2 |
| Fast Release | 5.0 | 5.59 | 574.9 |

Different ALV001 formulations were compared by adding them to gluten containing meals, incubating at 37° C. with or without mixing for 30 minutes, and measuring gluten degradation by gluten peptide ELISA. The results shown in the table below indicate that fast dissolving tablets, liquid formulations, and sprinkled granules all result in similar levels of substantial gluten degradation in a beaker. The results are expressed as the fold change in gluten degradation relative to placebo, and the fold change is the reciprocal of the fraction of gluten remaining in the sample. As shown in Table 8, the desired formulation showed about 10-fold change in gluten when tested in vitro at 30 minutes. The fast dissolving tablet showed 11-fold gluten degradation, and was useful within the 30 minute time period. While the slow dissolving tablet was less effective at degrading gluten over this time period, there are cases where it may be desirable to deliver at least a portion of the enzyme dose as a slow release tablet or particle. In particular, slow release tablets or particles are useful where the meal is eaten over a period of an hour or more or where a delay in the release by 10 to 60 minutes of an enzyme, in particular, a portion of ALV002, could improve its efficiency of degrading gluten fragments.

TABLE 8

Gluten Degradation by Different Formulations of ALV001 in Beaker (Fold-Change Relative to Placebo)

| Formulation | Beaker (fold change gluten degradation |
|---|---|
| Fast Dissolve Tablet | 11 |
| Slow Dissolve Tablet | 6.3 |
| Liquid Formulation | 14 |
| Sprinkled Granules | 9.9 |

Example 6

Exemplary Separate ALV001* and ALV002 Stickpacks with Separate Flavor Pack(s)

A quantitative composition of an exemplary ALV003 drug product is provided in Table 9 (quantities per stick pack, in mg); and for a range of flavor stickpacks in Table 10. The drug product is provided in 4 different strengths, i.e. 300 mg, 450 mg, 600 mg, and 900 mg. Since the ALV003 drug product is defined as a mixture of ALV001* and ALV002 enzymes in a 1:1 weight ratio (where the ALV001* weight is the weight of the corresponding amount of ALV001), separate stick packs for each dose include 50% of either the ALV001* enzyme or the ALV002 enzyme, which when combined result in the 4 different ALV003 doses (of 300 mg, 600 mg, 900 mg, and 1200 mg).

content can potentially reduce the duration of action of the enzyme, and the need to prevent this from unduly decreasing efficacy must be balanced against the flavorfulness of the dose to the patient. This table illustrates the interplay of these two variables, drink volume and buffer content, on the flavor formulation.

Those of skill in the art will appreciate that this example describes three unit doses, one for ALV001*, one for ALV002, and one for the flavorings/sweetener/other excipi-

TABLE 9

(ALV001* and ALV002 Drug Product Unit Doses)

| Active/Excipient | 300 mg | | 600 mg | | 900 mg | | 1200 mg | |
|---|---|---|---|---|---|---|---|---|
| | ALV001* | ALV002 | ALV001* | ALV002 | ALV001* | ALV002 | ALV001* | ALV002 |
| ALV001*# | 150 | 0 | 300 | 0 | 450 | 0 | 600 | 0 |
| ALV002 | 0 | 150 | 0 | 300 | 0 | 450 | 0 | 600 |
| Tris | 3.8 | 2.8 | 7.6 | 5.6 | 11.6 | 8.4 | 15.2 | 11.2 |
| Sucrose | 16.2 | 0 | 32.4 | 0 | 48.6 | 0 | 64.8 | 0 |
| EDTA | 6.4 | 4.0 | 12.8 | 8.0 | 19.2 | 12 | 25.6 | 16 |
| Mannitol | 32.0 | 22.0 | 64.0 | 44.0 | 96.0 | 66.0 | 128.0 | 88.0 |
| MTG | 0.6 | 1.0 | 1.2 | 2.0 | 2.0 | 2.8 | 2.4 | 4.0 |
| Sodium Citrate | 409.7 | 407.5 | 414.1 | 407.5 | 414.3 | 407.5 | 435.7 | 407.5 |
| Citric Acid | 111.7 | 92.5 | 131.7 | 92.5 | 149.1 | 92.5 | 171.3 | 92.5 |
| Sodium Metabisulfite | 8 | 0 | 8 | 0 | 8 | 0 | 8 | 0 |
| Total Mass/Stickpack | 738.4 | 679.8 | 971.8 | 859.6 | 1198.8 | 1039.0 | 1451.0 | 1219.2 |

In calculating the weight percentages of ALV001*, the ALV001* drug substance weight includes the contribution from the pro-peptide cleaved during the activation process.

The component quantities set forth in Table 9 include excipients contributed by the drug substance not required for function of the drug product. Specifically, such not required components include Tris, sucrose, mannitol, and EDTA.

TABLE 10

(Flavor/Excipient Pack Unit Dose)

| Excipient | Amount (mg) Low Volume & Low Buffer | Amount (mg) Low Volume & High Buffer (More Sour) | Amount (mg) High Volume & Low Buffer | Amount (mg) High Volume & High Buffer |
|---|---|---|---|---|
| Potassium citrate | 815 | 1565 | 815 | 1815 |
| Citric Acid | 185 | 352 | 185 | 440 |
| Cysteine | 100 | 100 | 100 | 100 |
| Sucralose | 65 | 65 | 50 | 50 |
| Flavor | 200-350 | 250-600 | 500 | 400-1000 |

The quantities provided in Table 10 are formulated for cysteine in the absence of a flavor masking coating. Where the cysteine is flavor masked, the sweetener (sucralose) and flavor components can be reduced as described above in the detailed description of the invention (i.e., from 2 to 5 fold each). In Table 10, a guide to adjust various buffer components and flavor for the type of flavor and solution volume are shown. In this table, a low volume of 100 ml and a high volume of 200 ml were used to prepare the drink, as the volume can have a substantial effect on the flavor, and adjusting the amount of flavor and sweetener added can markedly improve the taste of the dose for the patient. A second variable shown in the table is a high and low buffer content. The buffer may contribute a sour base flavor to the drink, and different flavors with more or less sourness may be preferred by some patients. Reduction of the buffer ents that collectively make a single unit dose of ALV003 in four different strengths (300 mg, 600 mg, 900 mg, and 1200 mg total enzyme). These unit doses may be dissolved/suspended in a potable liquid for immediate consumption by a celiac sprue patient at mealtime.

Example 7

Figure 6:
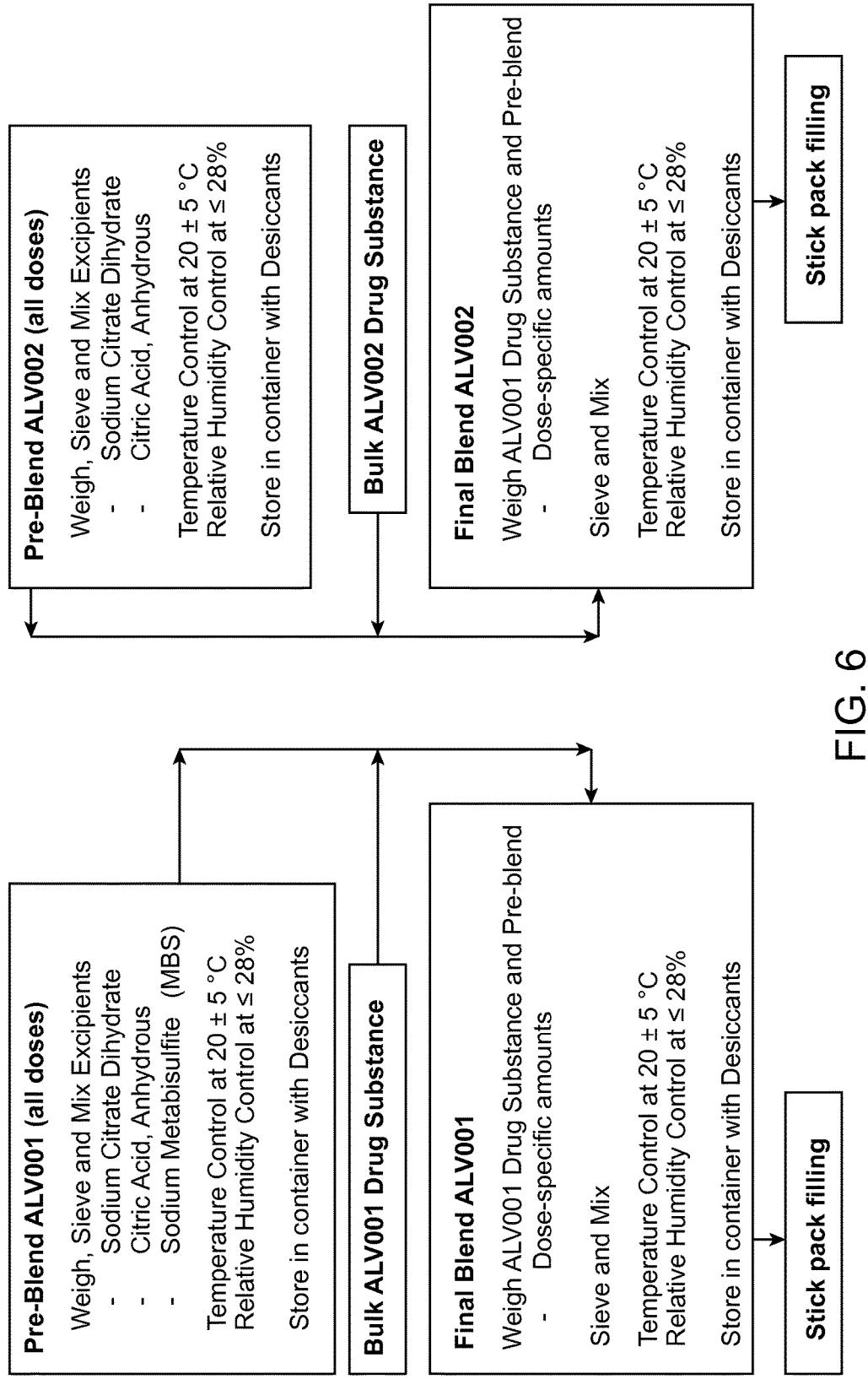
FIG. 6. Flow diagram for processing ALV003 drug product.

A process flow for drug product manufacture is shown in FIG. 6. Drug product manufacture was initiated by formulating a single pre-blend for all doses of ALV001, a single pre-blend for all doses of ALV002, and a single, final blend for placebo. The pre-blend for ALV001 contains 3 excipients, i.e. sodium citrate dihydrate, citric acid anhydrous, and sodium metabisulfite. First, citric acid and sodium metabisulfite were sieved together through a hand sieve, and subsequently mixed in a blender. Sodium citrate was then added, and the combined excipients were again mixed, followed by sieving and final mixing step. This pre-blending process was performed to ensure blend uniformity and to ensure that all doses of ALV001 formulation were identical with respect to excipient content. Moreover, the process was performed under controlled conditions to safeguard against degradation and moisture uptake.

The ALV002 pre-blend was prepared in the same manner as the ALV001 pre-blend, without sodium metabisulfite.

Following pre-blend manufacture, individual final blends for each dose of ALV001 and ALV002 were prepared, adjusting the amounts of drug product and pre-blend needed to be combined in order to formulate the exact dose strengths required (i.e. 100 mg, 300 mg, 450 mg, 600 mg and 900 mg, based on total enzyme content). The blending process was performed under the same controlled conditions as the pre-blend. The pre-blends were kept at ≤25° C., and the final blends are kept at 2-8° C., in a container with desiccants in an open polyethylene bag, until further use. Once individual dose strength final blends were available, these were subsequently filled into foil laminate stick packs on a single-line stick pack filler with continuous weight verification. Exemplary compositions are provided in Tables 11 and 12.

TABLE 11

| Quantitative composition of ALV003 drug product (quantities in mg) | | | | | | | | | | |
|---|---|---|---|---|---|---|---|---|---|---|
| | 100 mg Dose (50 mg each API) | | 300 mg Dose (150 mg each API) | | 450 mg Dose (225 mg each API) | | 600 mg Dose (300 mg each API) | | 900 mg Dose (450 mg each API) | |
| Active/ Excipient | ALV001* | ALV002 | ALV001* | ALV002 | ALV001* | ALV002 | ALV001* | ALV002 | ALV001* | ALV002 |
| ALV001* Drug Substance†# | 83 | 0 | 250 | 0 | 375 | 0 | 500 | 0 | 750 | 0 |
| ALV002 Drug Substance† | 0 | 83 | 0 | 250 | 0 | 375 | 0 | 500 | 0 | 750 |
| Sodium Metabisulfite | 8 | 0 | 8 | 0 | 8 | 0 | 8 | 0 | 8 | 0 |
| Na Citrate Dihydrate | 407.5 | 407.5 | 407.5 | 407.5 | 407.5 | 407.5 | 407.5 | 407.5 | 407.5 | 407.5 |
| Citric Acid Anhydrous | 92.5 | 92.5 | 92.5 | 92.5 | 92.5 | 92.5 | 92.5 | 92.5 | 92.5 | 92.5 |
| Total Mass per Stickpack | 591 | 583 | 758 | 750 | 883 | 875 | 1008 | 1000 | 1258 | 1250 |

†The drug substance quantities assume an enzyme content of 60%.
In calculating the weight percentages of ALV001*, the ALV001* drug substance weight includes the weight contributed by pro-peptide cleaved during the activation process.

TABLE 12

| Quantitative composition(quantities in mg) | | | | | | |
|---|---|---|---|---|---|---|
| Active/ | 100 mg | | 300 mg | | 450 mg | |
| Excipient | ALV001* | ALV002 | ALV001* | ALV002 | ALV001* | ALV002 |
| ALV001*# | 50 | 0 | 150 | 0 | 225 | 0 |
| ALV002 | 0 | 50 | 0 | 150 | 0 | 225 |
| Tris Base | 1 | 1 | 3 | 3 | 4.5 | 4.5 |
| Tris HCl | 0.83 | 0.83 | 2.5 | 2.5 | 3.75 | 3.75 |
| Sucrose | 3.58 | 0 | 10.75 | 0 | 16.13 | 0 |
| EDTA | 2.5 | 2.58 | 7.5 | 7.75 | 11.25 | 11.63 |
| Mannitol | 13.33 | 13.67 | 40 | 41 | 60 | 61.5 |
| NaCl | 0.17 | 0 | 0.5 | 0 | 0.75 | 0 |
| MTG | 0.33 | 0.33 | 1 | 1 | 1.5 | 1.5 |
| Sodium Citrate | 408.42 | 407.5 | 410.25 | 407.5 | 411.63 | 407.5 |
| Citric Acid | 101.67 | 92.5 | 120 | 92.5 | 133.75 | 92.5 |
| Sodium Metabisulfite | 8 | 0 | 8 | 0 | 8 | 0 |
| Total Mass/Stickpack | 589.83 | 568.41 | 753.5 | 705.25 | 876.26 | 807.88 |
| Active/ | 600 mg | | 900 mg | | 1200 mg | |
| Excipient | ALV001* | ALV002 | ALV001* | ALV002 | ALV001* | ALV002 |
| ALV001*# | 300 | 0 | 450 | 0 | 600 | 0 |
| ALV002 | 0 | 300 | 0 | 450 | 0 | 600 |
| Tris Base | 6 | 6 | 9 | 9 | 12 | 12 |
| Tris HCl | 5 | 5 | 7.5 | 7.5 | 10 | 10 |
| Sucrose | 21.5 | 0 | 32.25 | 0 | 43 | 0 |
| EDTA | 15 | 15.5 | 22.5 | 23.25 | 30 | 31 |
| Mannitol | 80 | 82 | 120 | 123 | 160 | 164 |
| NaCl | 1 | 0 | 1.5 | 0 | 2 | 0 |
| MTG | 2 | 2 | 3 | 3 | 4 | 4 |
| Sodium Citrate | 413 | 407.5 | 415.75 | 407.5 | 418.5 | 407.5 |

TABLE 12-continued

| Quantitative composition(quantities in mg) | | | | | | |
|---|---|---|---|---|---|---|
| Citric Acid | 147.5 | 92.5 | 175 | 92.5 | 202.5 | 92.5 |
| Sodium Metabisulfite | 8 | 0 | 8 | 0 | | |
| Total Mass/Stickpack | 999 | 910.5 | 1244.5 | 1115.75 | 1490 | 1321 |

In calculating the weight percentages of ALV001*, the ALV001* drug substance weight includes the weight contributed by pro-peptide cleaved during the activation process.

The component quantities set forth in Table 12 include excipients in the drug substance not required for the function of the drug product (sucrose, mannitol, and EDTA). In the above stickpacks, citric acid anhydrous and sodium citrate dihydrate were used. Other salts or hydrates may be substituted and the molar quantity of citrate in each component should be kept comparable to that disclosed in the Table 12. For example, the ALV002 stickpack with 100 mg ALV003 contains approximately 1.867 millimoles of citrate between the citric acid and sodium citrate, and approximately this amount should be contained if different salts or hydrates are to be substituted.

An exemplary quantitative composition of flavor packs is provided in Table 13 (quantities per pack, in grams).

TABLE 13

| Quantitative composition of flavor packs (quantities in grams) | | | |
|---|---|---|---|
| Component | Mango | Peach | Caramel |
| Citric Acid Anhydrous | 0.440 | 0.440 | 0.440 |
| Potassium Citrate Tribasic Monohydrate | 1.815 | 1.815 | 1.815 |
| L-Cysteine HCl Monohydrate | 0.100 | 0.100 | 0.100 |
| Sucralose | 0.050 | 0.050 | 0.050 |
| Flavor | 0.600 | 0.600 | 0.400 |
| Total Mass per Flavor Pack | 3.005 | 3.005 | 2.805 |

The quantities provided in Table 13 are formulated for cysteine in the absence of a flavor masking coating. Where the cysteine is flavor masked, the sweetener (sucralose) and flavor components can be reduced. Other salts or hydrates of the excipients, in particular, of citric acid, cysteine, or potassium citrate, can be used and the molar quantity should be comparable. For example, if citric acid monohydrate were used, a molar quantity of citrate of about 2.3 millimoles, which is comparable to the citrate in citric acid anhydrous could be substituted.

Figure 7:
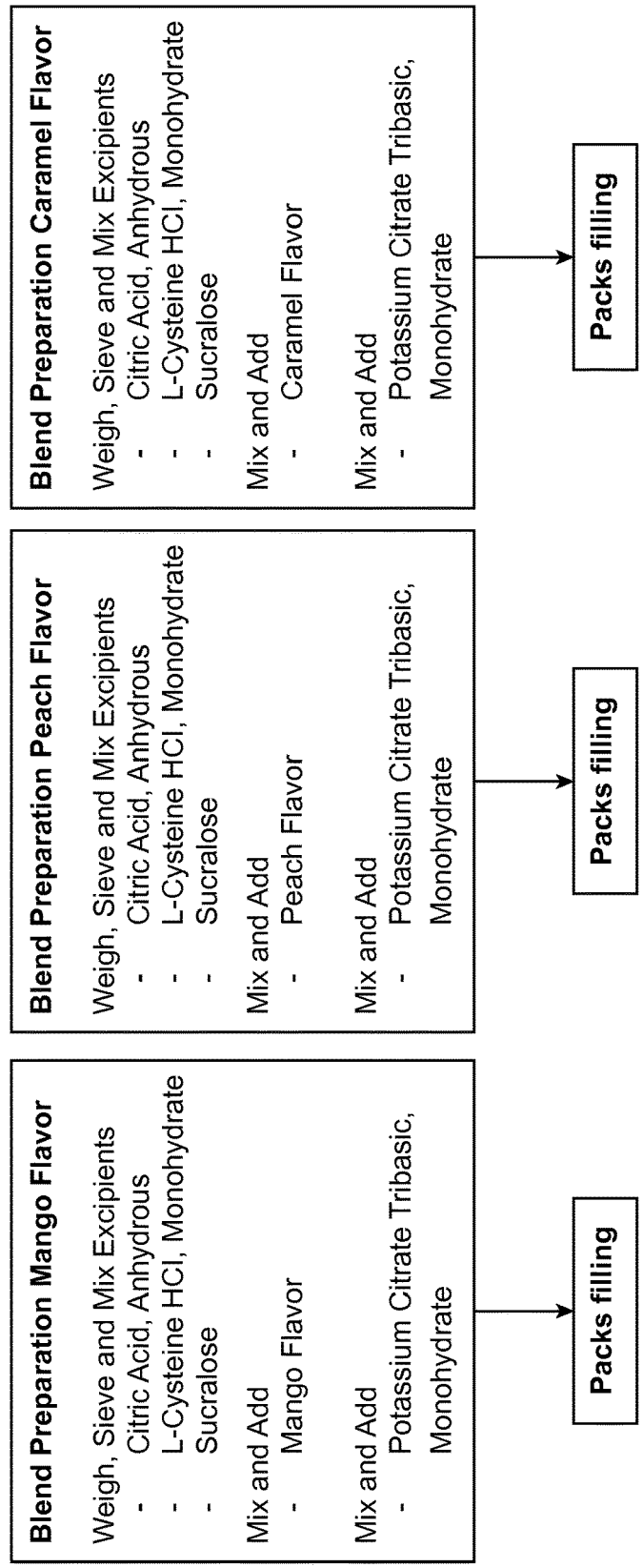
FIG. 7. Flow diagram for processing flavor pack.

Flavor packs were prepared as separate blends for each of the three flavors, which were subsequently filled into packs and labeled. The process flow for the flavor packs is shown in FIG. 7

Each flavor blend was prepared by first sieving the excipients citric acid anhydrous, potassium citrate tribasic monohydrate, L-cysteine HCL monohydrate, sucralose and flavor. Next, citric acid anhydrous, L-cysteine HCL monohydrate and sucralose were combined and mixed. Flavor was added in steps, followed by mixing after each addition. Potassium citrate tribasic monohydrate was added last. This blend was then filled into individual flavor packs.

Example 8

Combined ALV003 Stickpacks with Separate Flavor Packs

Foil laminate pouches to hold the combination ALV003 blends were hand heat-sealed on 3 sides. Combination packs of ALV001 and ALV002 were prepared for the ALV003 100 mg dose and for the 900 mg dose. These combination packs were prepared by combining the contents of the individual ALV001 and ALV002 stickpacks that were prepared in the previously described manufacture. The ALV003 100 mg dose was prepared by emptying the contents of one stickpack of ALV001 and one stickpack of ALV002 for the ALV003 100 mg dose into the foil laminate pouch. The pouch was purged with nitrogen and sealed by hand. The ALV003 900 mg dose was prepared by emptying the contents of one stickpack of ALV001 and one stickpack of ALV002 for the ALV003 900 mg dose into the foil laminate pouch. The pouch was purged with nitrogen and sealed by hand. All combination stickpacks were stored at room temperature.

TABLE 14

| ALV003 Combination Stickpacks | | | | | |
|---|---|---|---|---|---|
| Active/ Excipient | ALV003 100 mg | ALV003 300 mg | ALV003 450 mg | ALV003 600 mg | ALV003 900 mg |
| ALV001 | 50 | 150 | 225 | 300 | 450 |
| ALV002 | 50 | 150 | 225 | 300 | 450 |
| Tris Base | 2 | 6 | 9 | 12 | 18 |
| Tris HCl | 1.66 | 5 | 7.5 | 10 | 15 |
| Sucrose | 3.58 | 10.75 | 16.13 | 21.5 | 32.25 |
| EDTA | 5.08 | 15.25 | 22.88 | 30.5 | 45.75 |
| Mannitol | 27 | 81 | 121.5 | 162 | 243 |
| Sodium Chloride | 0.17 | 0.5 | 0.75 | 1 | 1.5 |
| MTG | 0.66 | 2 | 3 | 4 | 6 |
| Sodium Citrate | 815.92 | 817.75 | 819.13 | 820.5 | 823.25 |
| Citric Acid | 194.17 | 212.5 | 226.25 | 240 | 267.5 |
| Sodium Metabisulfite | 8 | 8 | 8 | 8 | 8 |
| Total Mass/ Stickpack | 1158.24 | 1458.75 | 1684.14 | 1909.5 | 2360.25 |

Example 9

ALV003 Gluten Degradation Test

Gluten degradation was performed with this formulation with Vegetable Korma meal (Amy's Kitchen). To simulate the fed gastric environment, simulated gastric fluid (SGF) is added at intervals before and after the meal. The effect of additional pepsin was also characterized.

The pH of the meal mixture during test was measured before and after each addition of SGF. Gluten degradation was analyzed by a competitive ELISA directed at the 33 mer epitope. The inclusion of pepsin and its absence in the simulated gastric fluid were compared.

Materials and Methods

TABLE 15

| | |
|---|---|
| K Citrate tribasic monohydrate | CAS 610-05-6, Product #25107, Sigma Aldrich |
| Na citrate dihydrate | CAS 6132-04-3, Cat # 777304, Macron Chemical (VWR) |
| Citric acid anhydrous | CAS 77-92-9, Cat# 0122-1, J. T. Baker (VWR) |
| L-Cysteine HCl | CAS 7048-04-6, Cat #2071-5, J. T. Baker (VWR) |
| Sodium Metabisulfite | CAS 7681-57-4, Cat #95035-862, Spectrum (VWR) |
| Tromethamine | CAS 77-86-1, Cat # 4102-01, J. T. Baker (VWR), Product # T6066, Sigma Aldrich |
| Tris HCl | CAS 1185-53-1, Cat #816124, M P Biochemicals |
| Edetate Disodium | CAS 6381-92-6, 7727-04, Macron Chemical (VWR) |
| Mannitol | CAS 69-65-8, BDH8009, VWR |
| Pepsin | CAS 9001-75-6, Product #P7012, Sigma Aldrich, ≥2,500 units/mg protein (E1%/280) |
| Guanidine Hydrochloride | CAS 50-01-1, Product # G4505, Sigma Aldrich |
| 2-mercaptoethanol | CAS 6024-2, Product # M6250, Sigma Aldrich |
| NaCl | CAS 7647-14-5, Cat # S641-212, Fisher Scientific |
| HCL | CAS 7647-01-0, Product # 258148, Sigma Aldrich |
| ALV001 | MP Code 40.007, Lot OP-013-F004 |
| ALV002 | MP Code 40.008, Lot OP-014-F004 |
| Flavor | Mango |

The values of pH in test meals with the 3 flavors were compared, and the flavors were found to have a negligible effect on pH when tested with the Vegetable Korma meal. Consequently, further testing was only done with mango flavor.

Solutions

TABLE 16

Placebo/flavor Buffer:

| Excipient | Quantity (mg) per 200 mL |
|---|---|
| K Citrate tribasic monohydrate | 1815 |
| Na citrate dihydrate | 821.4 |
| Citric acid anhydrous | 681.3 |
| L-Cysteine HCl | 100 |
| Sodium Metabisulfite | 8 |
| Tromethamine | 16 |
| Tris HCl | 14 |
| Edetate Disodium | 42 |
| Mannitol | 222 |
| Sucralose | 50 |
| Mango flavor | 600 |

TABLE 17

ALV003/flavor in buffer:

| Excipient | Quantity (mg) per 200 mL |
|---|---|
| K Citrate tribasic monohydrate | 1815 |
| Na citrate dehydrate | 815 |
| Citric acid anhydrous | 625 |
| L-Cysteine HCl | 100 |
| Sodium Metabisulfite | 8 |
| Sucralose | 50 |
| Mango flavor | 600 |
| ALV003 | 900 DS |
| ALV001 | 225 mg enzyme/dose/200 mL, dissolved in 200 mL ALV003 buffer |
| ALV002 | 225 mg enzyme/dose/200 mL, dissolved in 200 mL ALV003 buffer |

Simulated Gastric Fluid with pepsin: 0.2% w/v NaCl, 0.7% v/v HCl (VWR), pepsin 0.03%. Pepsin, 300 mg/L (2500 units)/L in simulated gastric fluid (USP 711 specifies the pepsin activity to be no more than 750,000 units/1000 mL dissolution solution).

Simulated Gastric Fluid without pepsin: 0.2% w/v NaCl, 0.7% v/v HCL (VWR); 2 times TGB 1M Tris, 4M Guanidine, 0.5M BME pH 7.7.

Meal Preparation: Heat the meal with a microwave according to the instructions on the box. 11.1 g of bread crumbs is added to the entire meal contents. Manually smash and cut to simulate chewing. Adjust the meal to 500 ml total volume by adding RO water. 1/10 of the total volume is used for each sample. Measure the sample and further divide the meal into 10%, 45%, and 45% by volume.

Methods

TABLE 18

Placebo with pepsin:

| | |
|---|---|
| T = 0 | 2 mL simulated gastric fluid with pepsin pH measurement |
| T = 0-1 | 5 mL meal heat to 37° C. |
| T = 1-3 | 10 mL placebo buffer |
| T = 3-8 | 22.5 mL meal |
| T = 8-15 | 4 mL simulated gastric fluid with pepsin, pH measurement |
| T = 15-17 | 10 mL placebo buffer |
| T = 17-22 | 22.5 mL meal |
| T = 22-29 | 4 mL simulated gastric fluid with pepsin, pH measurement |

Mix the contents in a 125 mL polypropylene (PP) bottle during and after each addition. Continue to incubate for a total of 45 minutes. Stop the incubation by adding 2 times TGB 1:1 (V:V). Incubate at 50° 'C for 1 hr.

TABLE 19

Placebo without pepsin:

| | |
|---|---|
| T = 0 | 2 mL simulated gastric fluid without pepsin pH measurement |
| T = 0-1 | 5 mL meal heat to 37°C. |
| T = 1-3 | 10 mL placebo buffer |
| T = 3-8 | 22.5 mL meal |
| T = 8-15 | 4 mL simulated gastric fluid without pepsin, pH measurement |
| T = 15-17 | 10 mL placebo buffer |
| T = 17-22 | 22.5 mL meal |
| T = 22-29 | 4 mL simulated gastric fluid without pepsin, pH measurement |

Mix the contents in a 125 mL PP bottle during and after each addition. Continue to incubate for a total of 45 minutes. Stop the incubation by adding 2 times TGB 1:1 (V:V). Incubate at 50'C for 1 hr.

TABLE 20

ALV003 with pepsin:

| | |
|---|---|
| T = 0 | 2 mL simulated gastric fluid with pepsin pH measurement |
| T = 0-1 | 5 mL meal heat to 37°C. |
| T = 1-3 | 10 mL ALV003 buffer |
| T = 3-8 | 22.5 mL meal |
| T = 8-15 | 4 mL simulated gastric fluid with pepsin, pH measurement |
| T = 15-17 | 10 mL ALV003 buffer |
| T = 17-22 | 22.5 mL meal |
| T = 22-29 | 4 mL simulated gastric fluid with pepsin, pH measurement |

Mix the contents in a 125 mL PP bottle during and after each addition. Continue to incubate for a total of 45 minutes. Stop the incubation by adding 2 times TGB 1:1 (V:V). Incubate at 50° C. for 1 hr.

TABLE 21

ALV003 without pepsin:

| | |
|---|---|
| T = 0 | 2 mL simulated gastric fluid without pepsin pH measurement |
| T = 0-1 | 5 mL meal heat to 37°C. |
| T = 1-3 | 10 mL ALV003 buffer |
| T = 3-8 | 22.5 mL meal |
| T = 8-15 | 4 mL simulated gastric fluid without pepsin, pH measurement |
| T = 15-17 | 10 mL ALV003 buffer |
| T = 17-22 | 22.5 mL meal |
| T = 22-29 | 4 mL simulated gastric fluid without pepsin, pH measurement |

Mix the contents in a 125 mL PP bottle during and after each addition. Continue to incubate for a total of 45 minutes. Stop the incubation by adding 2 times TGB 1:1 (V:V). Incubate at 50° C. for 1 hr. Repeat sample preparation and experiments for different meals.

TABLE 22

Placebo control with water (no gastric fluid)

| | |
|---|---|
| T = 0 | 2 mL water, pH measurement |
| T = 0-1 | 5 mL meal heat to 37°C. |
| T = 1-3 | 10 mL placebo buffer |
| T = 3-8 | 22.5 mL meal |
| T = 8-15 | 4 mL water, pH measurement |
| T = 15-17 | 10 mL placebo buffer |
| T = 17-22 | 22.5 mL meal |
| T = 22-29 | 4 mL water, pH measurement |

Mix the contents in a 125 mL PP bottle during and after each addition. Continue incubate to total 45 minutes. Stop the incubation. Add 2×TGB 1:1 (V:V). Incubate at 50'C for 1 hr.

TABLE 23

ALV003 Control with water (no gastric fluid)

| | |
|---|---|
| T = 0 | 2 mL water pH measurement |
| T = 0-1 | 5 mL meal heat to 37°C. |
| T = 1-3 | 10 mL ALV003 buffer |
| T = 3-8 | 22.5 mL meal |
| T = 8-15 | 4 mL water, pH measurement |
| T = 15-17 | 10 mL ALV003 buffer |
| T = 17-22 | 22.5 mL meal |
| T = 22-29 | 4 mL water, pH measurement |

Mix the contents in a 125 mL PP bottle during and after each addition. Continue to incubate for a total of 45 minutes. Stop the incubation by adding 2 times TGB 1:1 (V:V). Incubate at 50° C. for 1 hr.

Pipet 4 mL sample into a 15 mL PP tube after TGB extraction. Add 6 mL ETOH. Shake overnight. Centrifuge to obtain supernatant. Perform A1 ELISA.

Results

The range of pH values were 4.5 to 4.7 for vegetable korma meal as in Table 1 shown below. With the addition of water instead of SGF, the pH values were 5.1 to 5.3. The addition of pepsin had a negligible effect on pH.

TABLE 24 pH with Amy's gluten-free Indian Vegetable Korma

| | pH prior to addition of meal | pH after middle addition of SGF or Water | pH after final addition of SGF or Water | Final pH (5 min before end) |
|---|---|---|---|---|
| Placebo/pepsin | 1.3 | 4.6 | 4.7 | 4.7 |
| Placebo/no pepsin | 1.4 | 4.5 | 4.7 | 4.6 |
| Placebo/water+ | 5.5 | 5.0 | 5.1 | 5.1 |
| meal/ALV003/pepsin | 1.3 | 4.6 | 4.7 | 4.7 |
| meal/ALV003/no pepsin | 1.4 | 4.6 | 4.7 | 4.7 |
| meal/ALV003/water+ | 5.5 | 5.1 | 5.1 | 5.1 |

+Only water and not SGF was used for this treatment.

An antibody competitive ELISA method, directed to the 33 mer epitope, measured the remaining gluten in the tested samples. In this study, the gluten concentration of the placebos was used as a factor to determine the remaining gluten concentrations of the enzyme active meals. Thus, the percentage of the gluten degradation in ALV003 active samples was calculated by setting gluten concentration in placebo samples as 100%.

The placebo and the ALV003 enzyme active meal were prepared with pepsin added, pepsin free, and water only three groups. The mean values, SD, and CV % of the chromogenic absorbance from the ELISA assay in placebos and in enzyme active samples were calculated. The acceptable CV % was ≤12% in the same dilution levels and the repetitive samples The results of calculated percentages of gluten degradation by the ALV003 active enzyme were greater than 99% to 100% in the vegetable korma meal with or without pepsin. Using a series of gluten-free meals with known amounts of gluten added as bread crumbs in this model system, ALV003 degraded between 97 (meal of brown rice pasta with olive oil) and 100% of the gluten, and greater than 95% gluten degradation was consistent in this experimental design.

Example 10

ALV001 was activated in 50 mM acetate, pH 4.5 for 10 minutes at 37° C. prior to measuring the stability of the enzyme in different buffers.

The buffers (1 M glycine (pH 2.4), 1 M citrate (pH 3.1 & 3.6), and 1 M acetate (pH 4.5 & 4.9)) were prepared for testing the stability of activated ALV001. These buffers were diluted to 200 mM with water and pre-heated to 37° C. Activated ALV001 (ALV001*) was then added to each buffer, and aliquots were taken after 0.5, 2, 3.5, 6, 10, and 20 minutes to measure ALV001* activity over time. As shown in FIG. 8, ALV001* showed no activity in the 200 mM glycine buffer (pH 2.3) at the earliest time point. Further, the ALV001* completely lost detectable activity in the 200 mM citrate buffer (pH 3.0) by 6 minutes. ALV001* was fairly stable in buffers with pH 3.54-4.8 with a gradual loss of 25-55% activity over 20 minutes.

Although no buffers with a pH greater than 4.8 were tested, the enzyme activity assay was performed at pH 7.7 over the course of 1 minute with linear reaction kinetics suggesting the stability of activated ALV001* up to pH 7.7.

These data demonstrate that ALV001* is relatively unstable at pH below 3.5 at 37° C. In the pH range of 4 to 6, ALV001* remains stable for at least 20 minutes.

We claim:

1. A unit dosage form with ALV003 enzyme in an amount ranging from 100 mg to 6 g, wherein said unit dosage form is in three stickpacks:
   a first stickpack containing ALV001 or ALV001*, and 0.002-0.02 g sodium metabisulfite;
   a second stickpack containing ALV002;
   a third stickpack containing artificial sweetener, 0.01-0.1 g cysteine, a flavoring and 0.5-2 g potassium citrate;
   wherein the unit dose form comprises as excipients 0.5-2 g sodium citrate and 0.1-1 g citric acid split between said three stickpacks; and wherein said first and second stickpack do not comprise hygroscopic artificial sweeteners, cysteine and potassium citrate.

2. The unit dosage form of claim 1, wherein said unit dosage form contains between 0.5-2 g sodium citrate and 0.1-1 g citric acid, split between the first and second stickpacks and between 0.5-2 g potassium citrate and 0.01-0.1 g cysteine in the third stickpack.

3. The unit dosage form of claim 1, wherein the third stickpack comprises 0.01-0.5 g sucralose as artificial sweetener.

4. A unit dosage form of ALV003 divided into three stickpacks or sachets, wherein:
- a first stickpack or sachet comprises from 150 mg to no more than 600 mg of ALV001*;
- a second stickpack or sachet comprises from 150 mg to no more than 600 mg of ALV002;
- wherein the first and second stickpacks or sachets combined comprise from 204 mg to no more than 263 mg of citric acid, and from 817 mg to no more than 842 mg citrate present as a salt form; wherein 8 mg of sodium metabisulfite is present in said first stickpack or sachet; and wherein the total amount of sodium in the first and second stickpacks is no more than 800 mg; and
- a third stickpack or sachet comprising 0.3 to 200 mg artificial sweetener selected from sucralose, aspartame, and neotame, 25 to 1500 mg flavoring, 815 to 1815 mg potassium citrate, 185-440 mg citric acid, and about 100 mg cysteine;
- wherein the first and second stickpack or sachet do not comprise hygroscopic artificial sweetener, cysteine, and potassium citrate.

\* \* \* \* \*

SEQUENCE LISTING

<160> NUMBER OF SEQ ID NOS: 3

<210> SEQ ID NO 1
<211> LENGTH: 401
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

```
Met Gly Ser Ser His His His His His His Ser Ser Gly Leu Val Pro
1               5                   10                  15

Arg Gly Ser His Met Ala Ser Met Thr Gly Gln Gln Met Gly Arg
            20                  25                  30

Asp Pro Cys Ser Ala Ile Pro Met Glu Asp Lys Asp Leu Glu Ser Glu
            35                  40                  45

Glu Ala Leu Trp Asp Leu Tyr Glu Arg Trp Gln Ser Ala His Arg Val
        50                  55                  60

Arg Arg His His Ala Glu Lys His Arg Arg Phe Gly Thr Phe Lys Ser
65                  70                  75                  80

Asn Ala His Phe Ile His Ser His Asn Lys Arg Gly Asp His Pro Tyr
                85                  90                  95

Arg Leu His Leu Asn Arg Phe Gly Asp Met Asp Gln Ala Glu Phe Arg
            100                 105                 110

Ala Thr Phe Val Gly Asp Leu Arg Arg Asp Thr Pro Ser Lys Pro Pro
        115                 120                 125

Ser Val Pro Gly Phe Met Tyr Ala Ala Leu Asn Val Ser Asp Leu Pro
    130                 135                 140

Pro Ser Val Asp Trp Arg Gln Lys Gly Ala Val Thr Gly Val Lys Asp
145                 150                 155                 160

Gln Gly Lys Cys Gly Ser Cys Trp Ala Phe Ser Thr Val Val Ser Val
                165                 170                 175

Glu Gly Ile Asn Ala Ile Arg Thr Gly Ser Leu Val Ser Leu Ser Glu
            180                 185                 190

Gln Glu Leu Ile Asp Cys Asp Thr Ala Asp Asn Asp Gly Cys Gln Gly
        195                 200                 205

Gly Leu Met Asp Asn Ala Phe Glu Tyr Ile Lys Asn Asn Gly Gly Leu
    210                 215                 220

Ile Thr Glu Ala Ala Tyr Pro Tyr Arg Ala Ala Arg Gly Thr Cys Asn
225                 230                 235                 240

Val Ala Arg Ala Ala Gln Asn Ser Pro Val Val Val His Ile Asp Gly
                245                 250                 255

His Gln Asp Val Pro Ala Asn Ser Glu Glu Asp Leu Ala Arg Ala Val
            260                 265                 270

Ala Asn Gln Pro Val Ser Val Ala Val Glu Ala Ser Gly Lys Ala Phe
        275                 280                 285

Met Phe Tyr Ser Glu Gly Val Phe Thr Gly Glu Cys Gly Thr Glu Leu
    290                 295                 300

Asp His Gly Val Ala Val Val Gly Tyr Gly Val Ala Glu Asp Gly Lys
305                 310                 315                 320

Ala Tyr Trp Thr Val Lys Asn Ser Trp Gly Pro Ser Trp Gly Glu Gln
                325                 330                 335

Gly Tyr Ile Arg Val Glu Lys Asp Ser Gly Ala Ser Gly Gly Leu Cys
            340                 345                 350
```

```
Gly Ile Ala Met Glu Ala Ser Tyr Pro Val Lys Thr Tyr Ser Lys Pro
            355                 360                 365

Lys Pro Thr Pro Arg Arg Ala Leu Gly Ala Arg Glu Ser Leu Asn Ser
370                 375                 380

Ser Ser Val Asp Lys Leu Ala Ala Ala Leu Glu His His His His His
385                 390                 395                 400

His

<210> SEQ ID NO 2
<211> LENGTH: 262
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Ser Asp Leu Pro Pro Ser Val Asp Trp Arg Gln Lys Gly Ala Val
1               5                   10                  15

Thr Gly Val Lys Asp Gln Gly Lys Cys Gly Ser Cys Trp Ala Phe Ser
            20                  25                  30

Thr Val Val Ser Val Glu Gly Ile Asn Ala Ile Arg Thr Gly Ser Leu
        35                  40                  45

Val Ser Leu Ser Glu Gln Glu Leu Ile Asp Cys Asp Thr Ala Asp Asn
    50                  55                  60

Asp Gly Cys Gln Gly Gly Leu Met Asp Asn Ala Phe Glu Tyr Ile Lys
65                  70                  75                  80

Asn Asn Gly Gly Leu Ile Thr Glu Ala Ala Tyr Pro Tyr Arg Ala Ala
                85                  90                  95

Arg Gly Thr Cys Asn Val Ala Arg Ala Ala Gln Asn Ser Pro Val Val
            100                 105                 110

Val His Ile Asp Gly His Gln Asp Val Pro Ala Asn Ser Glu Glu Asp
        115                 120                 125

Leu Ala Arg Ala Val Ala Asn Gln Pro Val Ser Val Ala Val Glu Ala
    130                 135                 140

Ser Gly Lys Ala Phe Met Phe Tyr Ser Glu Gly Val Phe Thr Gly Glu
145                 150                 155                 160

Cys Gly Thr Glu Leu Asp His Gly Val Ala Val Gly Tyr Gly Val
                165                 170                 175

Ala Glu Asp Gly Lys Ala Tyr Trp Thr Val Lys Asn Ser Trp Gly Pro
                180                 185                 190

Ser Trp Gly Glu Gln Gly Tyr Ile Arg Val Glu Lys Asp Ser Gly Ala
            195                 200                 205

Ser Gly Gly Leu Cys Gly Ile Ala Met Glu Ala Ser Tyr Pro Val Lys
        210                 215                 220

Thr Tyr Ser Lys Pro Lys Pro Thr Pro Arg Arg Ala Leu Gly Ala Arg
225                 230                 235                 240

Glu Ser Leu Asn Ser Ser Ser Val Asp Lys Leu Ala Ala Ala Leu Glu
                245                 250                 255

His His His His His His
            260

<210> SEQ ID NO 3
<211> LENGTH: 741
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Met Val Ser Ser His His His His His Ser Ser Gly Leu Val Pro
1               5                   10                  15

Arg Gly Ser Lys Asn Arg Leu Trp Leu Ala Met Ala Ala Pro Leu Ala
            20                  25                  30

Leu Ala Thr Pro Val Ala Phe Ala Gln Thr Pro Thr Leu Ala Lys
            35                  40                  45

Asp Gln Ala Met Pro Ser Leu Pro Pro Tyr Pro Ala Ser Pro Gln Val
    50                  55                  60

Pro Leu Val Glu Asp His Phe Gly Glu Lys Val Ser Asp Pro Trp Arg
65                  70                  75                  80

Trp Leu Glu Ala Asp Val Arg Thr Asp Ala Lys Val Ala Ala Trp Val
                85                  90                  95

Gln Ala Gln Ser Ala Tyr Thr Ala Ala Tyr Leu Lys Gln Leu Pro Glu
            100                 105                 110

Arg Ala Ala Leu Glu Lys Arg Met Lys Ala Leu Ile Asp Tyr Glu Arg
            115                 120                 125

Phe Gly Leu Pro Gln Arg Arg Gly Ala Ser Val Phe Tyr Ser Trp Asn
    130                 135                 140

Ser Gly Leu Met Asn Gln Ser Gln Leu Leu Val Arg Pro Ala Asp Ala
145                 150                 155                 160

Pro Val Gly Thr Lys Gly Arg Val Leu Leu Asp Pro Asn Thr Trp Ala
                165                 170                 175

Lys Asp Gly Ala Thr Ala Leu Asp Ala Trp Ala Ala Ser Asp Asp Gly
            180                 185                 190

Arg Leu Leu Ala Tyr Ser Val Gln Asp Gly Gly Ser Asp Trp Arg Thr
            195                 200                 205

Val Lys Phe Val Gly Val Ala Asp Gly Lys Pro Leu Ala Asp Glu Leu
    210                 215                 220

Lys Trp Val Lys Phe Ser Gly Leu Ala Trp Leu Gly Asn Asp Ala Leu
225                 230                 235                 240

Leu Tyr Ser Arg Phe Ala Glu Pro Lys Glu Gly Gln Ala Phe Gln Ala
                245                 250                 255

Leu Asn Tyr Asn Gln Thr Val Trp Leu His Arg Leu Gly Thr Pro Gln
            260                 265                 270

Ser Ala Asp Gln Pro Val Phe Ala Thr Pro Glu Leu Pro Lys Arg Gly
            275                 280                 285

His Gly Ala Ser Val Ser Ser Asp Gly Arg Trp Val Val Ile Thr Ser
    290                 295                 300

Ser Glu Gly Thr Asp Pro Val Asn Thr Val His Val Ala Arg Val Thr
305                 310                 315                 320

Asn Gly Lys Ile Gly Pro Val Thr Ala Leu Ile Pro Asp Leu Lys Ala
                325                 330                 335

Gln Trp Asp Phe Val Asp Gly Val Asp Gln Leu Trp Phe Val Ser
            340                 345                 350

Gly Asp Gly Ala Pro Leu Lys Lys Ile Val Arg Val Asp Leu Ser Gly
            355                 360                 365

Ser Thr Pro Arg Phe Asp Thr Val Pro Glu Ser Lys Asp Asn Leu
    370                 375                 380

-continued

```
Glu Ser Val Gly Ile Ala Gly Asn Arg Leu Phe Ala Ser Tyr Ile His
385                 390                 395                 400

Asp Ala Lys Ser Gln Val Leu Ala Phe Asp Leu Asp Gly Lys Pro Ala
            405                 410                 415

Gly Ala Val Ser Leu Pro Gly Ile Gly Ser Ala Ser Gly Leu Ser Gly
            420                 425                 430

Arg Pro Gly Asp Arg His Ala Tyr Leu Ser Phe Ser Ser Phe Thr Gln
        435                 440                 445

Pro Ala Thr Val Leu Ala Leu Asp Pro Ala Thr Ala Lys Thr Thr Pro
    450                 455                 460

Trp Glu Pro Val His Leu Thr Phe Asp Pro Ala Asp Phe Arg Val Glu
465                 470                 475                 480

Gln Val Phe Tyr Pro Ser Lys Asp Gly Thr Lys Val Pro Met Phe Ile
                485                 490                 495

Val Arg Arg Lys Asp Ala Lys Gly Pro Leu Pro Thr Leu Leu Tyr Gly
            500                 505                 510

Tyr Gly Gly Phe Asn Val Ala Leu Thr Pro Trp Phe Ser Ala Gly Phe
        515                 520                 525

Met Thr Trp Ile Asp Ser Gly Gly Ala Phe Ala Leu Ala Asn Leu Arg
    530                 535                 540

Gly Gly Gly Glu Tyr Gly Asp Ala Trp His Asp Ala Gly Arg Arg Asp
545                 550                 555                 560

Lys Lys Gln Asn Val Phe Asp Asp Phe Ile Ala Ala Gly Glu Trp Leu
                565                 570                 575

Ile Ala Asn Gly Val Thr Pro Arg His Gly Leu Ala Ile Glu Gly Gly
            580                 585                 590

Ser Asn Gly Gly Leu Leu Ile Gly Ala Val Thr Asn Gln Arg Pro Asp
        595                 600                 605

Leu Phe Ala Ala Ala Ser Pro Ala Val Gly Val Met Asp Met Leu Arg
    610                 615                 620

Phe Asp Gln Phe Thr Ala Gly Arg Tyr Trp Val Asp Asp Tyr Gly Tyr
625                 630                 635                 640

Pro Glu Lys Glu Ala Asp Trp Arg Val Leu Arg Arg Tyr Ser Pro Tyr
                645                 650                 655

His Asn Val Arg Ser Gly Val Asp Tyr Pro Ala Ile Leu Val Thr Thr
            660                 665                 670

Ala Asp Thr Asp Asp Arg Val Val Pro Gly His Ser Leu Lys Tyr Thr
        675                 680                 685

Ala Ala Leu Gln Thr Ala Ala Ile Gly Pro Lys Pro His Leu Ile Arg
    690                 695                 700

Ile Glu Thr Arg Ala Gly His Gly Ser Gly Lys Pro Ile Asp Lys Gln
705                 710                 715                 720

Ile Glu Glu Thr Ala Asp Val Gln Ala Phe Leu Ala His Phe Thr Gly
                725                 730                 735

Leu Thr Pro Arg Pro
            740
```